US012569943B2

(12) United States Patent
Okuma et al.

(10) Patent No.: US 12,569,943 B2
(45) Date of Patent: Mar. 10, 2026

(54) REPAIR WELDING DEVICE AND REPAIR WELDING METHOD

(71) Applicant: Panasonic Intellectual Property Management Co., Ltd., Osaka (JP)

(72) Inventors: Katsuaki Okuma, Osaka (JP); Ryutaro Monden, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 831 days.

(21) Appl. No.: 17/832,896

(22) Filed: Jun. 6, 2022

(65) Prior Publication Data

US 2022/0297246 A1 Sep. 22, 2022

Related U.S. Application Data

(63) Continuation of application No. PCT/JP2020/040776, filed on Oct. 30, 2020.

(30) Foreign Application Priority Data

Dec. 6, 2019 (JP) ................................. 2019-221253

(51) Int. Cl.
*B23K 37/02* (2006.01)
*B23K 9/12* (2006.01)
(Continued)

(52) U.S. Cl.
CPC ............ *B23K 37/0229* (2013.01); *B23K 9/12* (2013.01); *B23K 31/125* (2013.01); *G01N 21/95* (2013.01);
(Continued)

(58) Field of Classification Search
CPC .... B23K 9/12; B23K 31/125; B23K 37/0229; G01N 21/95; G01N 33/207; G01N 33/2045
See application file for complete search history.

(56) References Cited

U.S. PATENT DOCUMENTS

| | | | | |
|---|---|---|---|---|
| 2020/0276674 A1* | 9/2020 | Lee | ...................... | B23K 31/125 |
| 2022/0097178 A1* | 3/2022 | Mohri | .................... | B23K 9/095 |
| 2022/0297246 A1* | 9/2022 | Okuma | ................ | B23K 26/032 |

FOREIGN PATENT DOCUMENTS

| | | |
|---|---|---|
| CN | 104439704 | 3/2015 |
| CN | 105081528 | 11/2015 |

(Continued)

OTHER PUBLICATIONS

Machine Translation of Shimizu, JP 2010-253538, performed on Jun. 4, 2025 (Year: 2010).*

(Continued)

*Primary Examiner* — Brian W Jennison
(74) *Attorney, Agent, or Firm* — Wenderoth, Lind & Ponack, L.L.P.

(57) ABSTRACT

A repair welding device includes an inspection result acquisition unit configured to acquire an appearance inspection result including information about a defective portion of a weld bead of a welded workpiece produced by a main welding that is executed by a welding robot, and a robot control unit configured to instruct the welding robot to execute a repair welding on a position of the defective portion using the appearance inspection result based on a relationship between the position of the defective portion and a predetermined width related to the weld bead.

7 Claims, 13 Drawing Sheets

(51) Int. Cl.
| | |
|---|---|
| B23K 31/12 | (2006.01) |
| G01N 21/95 | (2006.01) |
| G01N 33/2045 | (2019.01) |
| G01N 33/207 | (2019.01) |

(52) U.S. Cl.
CPC ....... G01N 33/2045 (2019.01); G01N 33/207 (2019.01)

(56) References Cited

FOREIGN PATENT DOCUMENTS

| | | |
|---|---|---|
| CN | 107931802 | 4/2018 |
| JP | 7-132372 | 5/1995 |
| JP | 2000-167666 | 6/2000 |
| JP | 2012-37487 | 2/2012 |
| WO | 2019/017071 | 1/2019 |
| WO | 2019/078375 | 4/2019 |

OTHER PUBLICATIONS

Extended European Search Report issued Jun. 14, 2023 in corresponding European Patent Application No. 20897562.3.
International Search Report issued Dec. 28, 2020 in corresponding International Application No. PCT/JP2020/040776.
Office Action dated Dec. 23, 2025 in corresponding Indian Application No. 202247031865.
Eirik B. Njaastad et al., "Automatic Touch-Up Welding Paths Using 3D Vision", 2016, Science Direct, pp. 73-78, https://doiorg/10.1016/j.ifacol.2016.12.164.
Luciane Baldassari Soares et al., "Computer Vision System for Weld Bead Analysis", 2018, Proceedings of the 13th International Joint Conference Vision, Imaging and Computer Graphics Theory and Applications (VISIGRAPP 2018), vol. 4, pp. 402-409, https://www.scitepress.org/papers/2018/66260/66260.pdf.

* cited by examiner d1<W1

S1: START DETECTED SPOT
E1: END DETECTED SPOT

*FIG. 5* d2>W1

WLN2

AR2

E2

RPW2

S2 d2

W1

2W1

BD2

S2: START DETECTED SPOT
E2: END DETECTED SPOT

GENERATION OF REPAIR WELDING PROGRAM

REPAIR WELDING DEVICE AND REPAIR WELDING METHOD

CROSS-REFERENCE TO RELATED APPLICATIONS

This is a continuation of International Application No. PCT/JP2020/040776 filed on Oct. 30, 2020, and claims priority from Japanese Patent Application No. 2019-221253 filed on Dec. 6, 2019, the entire content of which is incorporated herein by reference.

TECHNICAL FIELD

The present disclosure relates to a repair welding device and a repair welding method.

BACKGROUND ART

JP-A-2012-37487 discloses a shape inspection device that projects slit light onto a weld bead, images shape lines sequentially formed on the weld bead by scanning the weld bead with the slit light, and acquires a three-dimensional shape of the weld bead as point cloud data based on imaging data of the sequentially formed shape lines. The shape inspection device sets a cutting line different from the shape lines formed by scanning the weld bead with the slit light to the weld bead displayed based on the point cloud data in accordance with an input, and calculates a cross-sectional shape of the weld bead at the cutting line based on the point cloud data corresponding to the cutting line. The shape inspection device compares various feature amounts calculated according to the cross-sectional shape with allowable ranges of the various feature amounts registered in advance, and determines whether the feature amounts are good or poor.

SUMMARY OF INVENTION

The present disclosure provides a repair welding device and a repair welding method for more efficiently repairing and welding a defective portion of a welded workpiece produced by a main welding.

Aspect of non-limiting embodiments of the present disclosure relates to a repair welding device. The repair welding device includes an inspection result acquisition unit configured to acquire an appearance inspection result including information about a defective portion of a weld bead of a welded workpiece produced by a main welding executed by a welding robot, and a robot control unit configured to instruct the welding robot to execute a repair welding on a position of the defective portion using the appearance inspection result based on a relationship between the position of the defective portion and a predetermined width related to the weld bead.

Aspect of non-limiting embodiments of the present disclosure relates to a repair welding method to be executed by a repair welding device. The repair welding method includes a process of acquiring an appearance inspection result including information about a defective portion of a weld bead of a welded workpiece produced by a main welding executed by a welding robot, and a process of instructing the welding robot to execute a repair welding on a position of the defective portion using the appearance inspection result based on a relationship between the position of the defective portion and a predetermined width related to the weld bead.

According to the present disclosure, a defective portion of a welded workpiece produced by a main welding can be more efficiently repaired and welded.

BRIEF DESCRIPTION OF DRAWINGS

FIG. 5 is a diagram schematically showing a second operation outline example related to specification of a repaired and welded portion corresponding to a detected spot region obtained by an appearance inspection.

Figure 1:
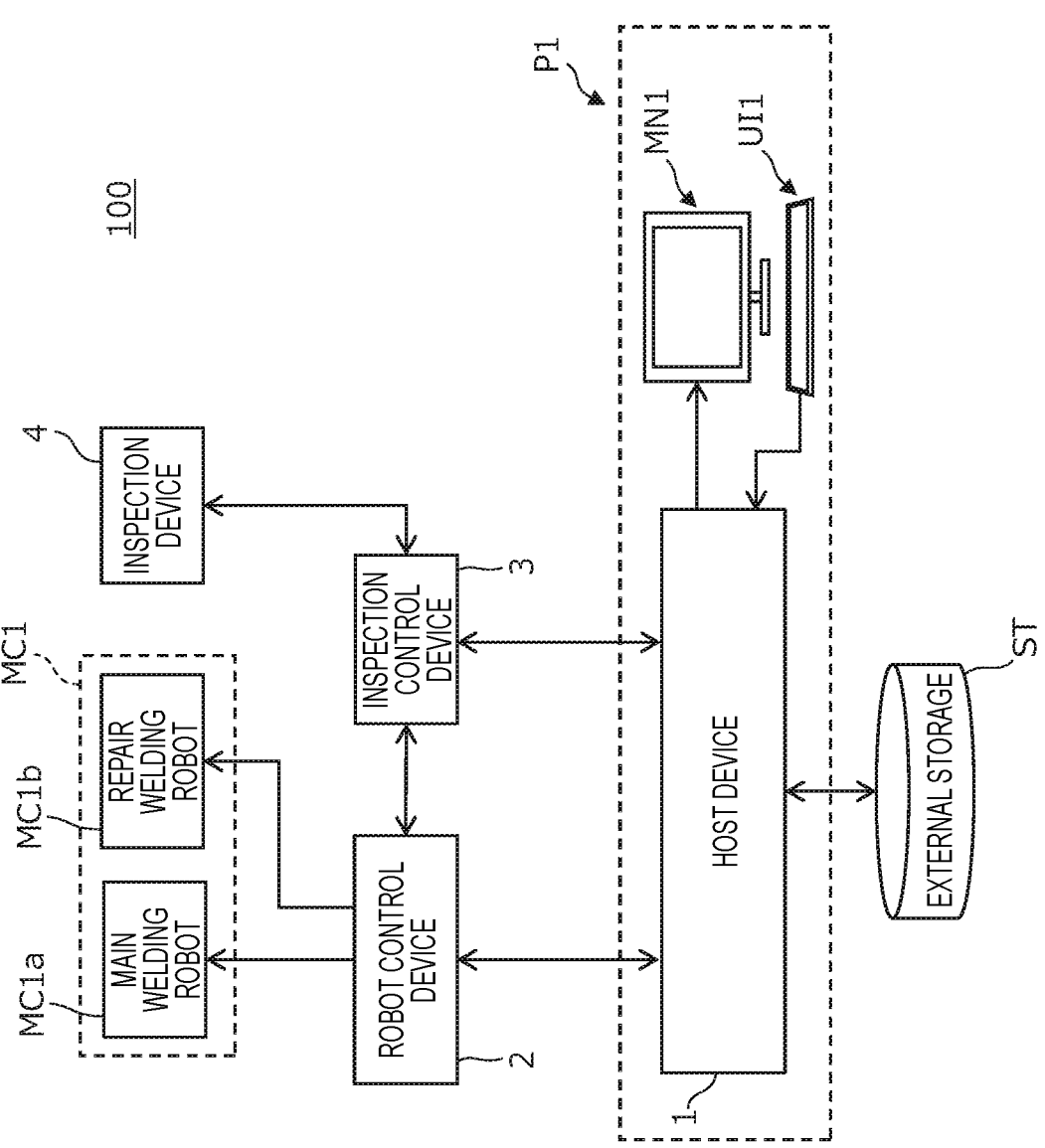
FIG. 1 is a schematic diagram showing a system configuration example of a welding system.

DESCRIPTION OF EMBODIMENTS (Background of the Present Disclosure)

The related art including JP-A-2012-37487 does not disclose a technique in which a welding robot or the like automatically executes a repair welding in order to correct (repair) a portion where a welding defect (that is, a defect) occurs based on an appearance inspection result of a workpiece (hereinafter, referred to as a "welded workpiece") produced by a main welding. In order to automatically execute a repair welding by the welding robot, it is required to prepare in advance a program for the repair welding in which a portion where the repair welding is to be executed is specified in a similar manner to the main welding. In order to prevent interference between a tip end portion of the welding robot and the welded workpiece or a jig for fixing the welded workpiece while actually executing a repair welding on a welding defective portion, it is preferable to generate a repair welding program by partially changing a main welding program that is generated to produce the welded workpiece. In other words, an operation of the welding robot during the repair welding can be stabilized by skillfully using an operation trajectory of the welding robot during the main welding.

In an appearance inspection of the welded workpiece, information (for example, coordinates) related to a position of a welding defective portion (hereinafter, simply referred to as a "defective portion") is detected by an inspection device such as a camera or a sensor that projects laser light, and the information is output as defective portion information. Therefore, in order to generate the repair welding program described above, it is required to specifically specify which welding section of the main welding program corresponds to the defective portion. However, for example, when a weld bead formed by the main welding is thick or when there is a slight error in positional accuracy of the defective portion output from the inspection device, the defective portion information detected by the inspection device may not necessarily be positioned on the operation trajectory of the welding robot defined in the main welding program. On the other hand, when the defective portion detected by the inspection device is located at a position considerably far from a welding line defined by the main welding program, the defective portion may not be sufficiently repaired only by repairing and welding a corresponding point on the welding line. Therefore, when the welding robot automatically executes a repair welding, it is required to specify a section to be repaired and welded with high accuracy depending on a position of a defective portion obtained by an appearance inspection. An example of a repair welding device and a repair welding method for more efficiently repairing and welding a defective portion of a welded workpiece produced by a main welding will be described in the following embodiments.

Hereinafter, embodiments specifically disclosing a repair welding device and a repair welding method according to the present disclosure will be described in detail with reference to the drawings as appropriate. However, unnecessarily detailed description may be omitted.

For example, detailed description of a well-known matter or repeated description of substantially the same configuration may be omitted. This is to avoid unnecessary redundancy in the following description and to facilitate understanding of those skilled in the art. It should be noted that the accompanying drawings and the following description are provided to enable those skilled in the art to fully understand the present disclosure, and are not intended to limit the range of the claims.

First Embodiment

A repair welding device according to the first embodiment acquires an appearance inspection result including information about a defective portion of a weld bead of a welded workpiece produced by a main welding executed by a welding robot, and instructs the welding robot to execute a repair welding on a position of the defective portion using the appearance inspection result based on a relationship between the position of the defective portion and a predetermined width related to the weld bead. Hereinafter, a workpiece to be welded by a main welding is defined as an "original workpiece", a workpiece produced (manufactured) by the main welding is defined as a "welded workpiece", and a workpiece of which a detected welding defective portion of the "welded workpiece" is repaired and welded is defined as a "repaired and welded workpiece". A process of producing a welded workpiece by joining an original workpiece and another original workpiece by a welding robot or the like is defined as a "main welding", and a process of correcting (repairing) a defective portion of the welded workpiece by a welding robot or the like is defined as a "repair welding". The "welded workpiece" or the "repaired and welded workpiece" is not limited to a workpiece produced by the main welding executed once, and may be a composite workpiece produced the main welding executed two or more times.

(Configuration of Welding System)

FIG. 1 is a schematic diagram showing a system configuration example of a welding system 100. The welding system 100 includes a host device 1 connected to an external storage ST, an input interface UI1, a monitor MN1, a robot control device 2, an inspection control device 3, a main welding robot MC1a, and a repair welding robot MC1b. The main welding robot MC1a and the repair welding robot MC1b may be configured as separate robots, or may be configured as the same welding robot MC1. In order to facilitate the understanding of the following description, it is assumed that both a main welding and a repair welding are executed by the welding robot MC1. Although only one pair of the robot control device 2 and the main welding robot MC1a, the repair welding robot MC1b is shown in FIG. 1, a plurality of such pairs may be provided. The welding system 100 may further include an inspection device 4.

The host device 1 serving as an example of a repair welding device integrally controls, via the robot control device 2, the execution of a main welding (for example, start and completion of the main welding) executed by the welding robot MC1. For example, the host device 1 reads out welding related information input or set in advance by a user (for example, a welding operator or a system administrator. The same applies hereinafter.) from the external storage ST, generates a main welding execution command including contents of the welding related information by using the welding related information, and transmits the main welding execution command to the corresponding robot control device 2. When the main welding executed by the welding robot MC1 is completed, the host device 1 receives a main welding completion report indicating that the main welding executed by the welding robot MC1 is completed from the robot control device 2, updates a status of a corresponding original workpiece to a status indicating that the main welding is completed, and records the status in the external storage ST. The main welding execution command described above is not limited to being generated by the host device 1, and may be generated by, for example, an operation panel (for example, a programmable logic controller (PLC)) of equipment in a factory or the like where the main welding is executed, or an operation panel (for example, a teach pendant (TP)) of robot control devices 2a, 2b, and the like. The teach pendant (TP) is a device for operating the main welding robot MC1a, the repair welding robot MC1b, and the like that are connected to the robot control devices 2a, 2b, and the like.

The host device 1 integrally controls, via the inspection control device 3, the execution of an appearance inspection (for example, start and completion of the appearance inspection) executed by the inspection device 4. For example, when the host device 1 receives the main welding completion report from the robot control device 2, the host device 1 generates an appearance inspection execution command for a welded workpiece produced by the welding robot MC1, and transmits the appearance inspection execution command to the inspection control device 3. When the appearance inspection executed by the inspection device 4 is completed, the host device 1 receives an appearance inspection report indicating that the appearance inspection executed by the inspection device 4 is completed from the inspection control device 3, updates the status to a status indicating that the appearance inspection of the welded workpiece is completed, and records the status in the external storage ST.

The host device 1 integrally controls, via the robot control device 2, the execution of a repair welding (for example, start and completion of the repair welding) executed by the welding robot MC1. For example, when the host device 1 receives the appearance inspection report from the inspection control device 3, the host device 1 generates a repair welding execution command for the welded workpiece produced by the welding robot MC1, and transmits the repair welding execution command to the robot control device 2. When a repair welding executed by the welding robot MC1 is completed, the host device 1 receives a repair welding completion report indicating that the repair welding executed by the welding robot MC1 is completed from the robot control device 2, updates the status to a status indicating that the repair welding for a corresponding welded workpiece is completed, and records the status in the external storage ST.

Here, the welding related information is information indicating contents of the main welding executed by the welding robot MC1. The welding related information is generated in advance for each process of the main welding and is registered in the external storage ST. The welding related information includes, for example, the number of original workpieces used in the main welding, workpiece information including an ID, a name, and a welded portion of an original workpiece used in the main welding, a scheduled execution date on which the main welding is executed, the number of welded workpieces to be produced, and various welding conditions during the main welding. The welding related information is not limited to data of items described above. Based on an execution command transmitted from the host device 1, the robot control device 2 causes the welding robot MC1 to execute a main welding using a plurality of original workpieces designated by the execution command. The welding related information described above is not limited to being managed by the host device 1 with reference to the external storage ST, and may be managed by, for example, the robot control device 2. In this case, since the robot control device 2 can know the completion of the main welding, the robot control device 2 may manage an actual execution date instead of the scheduled execution date on which a welding process is scheduled to be executed in the welding related information. A type of the main welding is not limited in the present specification, and a process of joining a plurality of original workpieces will be described as an example in order to make the description easy to understand. There may be a process of melting an arc welding rod and flowing the melted arc welding rod into a welded portion of one original workpiece (for example, a base material), or another welding may be used.

The host device 1 is connected to the monitor MN1, the input interface UI1, and the external storage ST so that the host device 1 can input data into and output data to the monitor MN1, the input interface UI1, and the external storage ST. The host device 1 is further connected to the robot control device 2 so that data can be communicated between the host device 1 and the robot control device 2. The host device 1 may include a terminal device P1 that includes the monitor MN1 and the input interface UI1 in an integrated manner, and may further include the external storage ST in an integrated manner. In this case, the terminal device P1 is a personal computer (PC) that is used by a user before the main welding is executed.

The terminal device P1 is not limited to the PC described above, and may be a computer device having a communication function, such as a smartphone or a tablet terminal.

The monitor MN1 may be configured with a display device such as a liquid crystal display (LED) or an organic electroluminescence (EL). The monitor MN1 may display, for example, a screen including a notification indicating that a main welding is completed or a notification indicating that a repair welding is completed and the notification is output from the host device 1. Instead of the monitor MN1, a speaker (not shown) may be connected to the host device 1, or the monitor MN1 and a speaker (not shown) may be connected to the host device 1. The host device 1 may output, via the speaker, a notification indicating that a main welding is completed or a sound indicating that a repair welding is completed.

The input interface UI1 is a user interface that detects an input operation of a user and outputs the input operation to the host device 1, and may be configured with, for example, a mouse, a keyboard, a touch panel, or the like. The input interface UI1 receives, for example, an input operation when a user generates welding related information or an input operation when a main welding execution command is transmitted to the robot control device 2.

The external storage ST is configured with, for example, a hard disk drive or a solid state drive. The external storage ST stores, for example, data of welding related information generated for each main welding, and workpiece information (see above description) of a welded workpiece produced by a main welding or a repaired and welded workpiece repaired by a repair welding.

The robot control device 2 serving as an example of a repair welding device is connected to the host device 1 so that data can be communicated between the robot control device 2 and the host device 1, and the robot control device 2 is connected to the welding robot MC1 so that data can be communicated between the robot control device 2 and the welding robot MC1. When the robot control device 2 receives the main welding execution command transmitted from the host device 1, the robot control device 2 controls the corresponding welding robot MC1 based on the main welding execution command to execute a main welding. When the robot control device 2 detects that the main welding is completed, the robot control device 2 generates a main welding completion report indicating that the main welding is completed, and notifies the host device 1 of the main welding completion report. Accordingly, the host device 1 can appropriately detect the completion of the main welding based on the report transmitted from the robot control device 2. A method of detecting the completion of a main welding by the robot control device 2 may be, for example, a method of determining the completion of a main welding based on a signal indicating the completion of a main welding from a sensor (not shown) provided in a wire feeding device 300, or may be a known method, and contents of the method of detecting the completion of a main welding is not limited.

When the robot control device 2 receives an appearance inspection program execution command transmitted from the host device 1, the robot control device 2 controls the corresponding welding robot MC1 based on the appearance inspection program execution command to execute an appearance inspection in accordance with an appearance inspection program included in the appearance inspection program execution command. In the welding system 100 according to the first embodiment, since the inspection device 4 is attached to the welding robot MC1 (see following description), during an appearance inspection, the welding robot MC1 (in other words, the inspection device 4) scans a welded workpiece on which the appearance inspection is to be executed and acquires shape data, and at the same time, the welding robot MC1 moves under the control of the robot control device 2. When the inspection device 4 is not attached to the welding robot MC1, the inspection device 4 only needs to scan a welded workpiece on which an appearance inspection is to be executed and acquire shape data. When the robot control device 2 detects the completion of the movement of the welding robot MC1 (in other words, the inspection device 4), the robot control device 2 may generate a notification indicating that the movement of the inspection device 4 is completed and transmit the notification to the inspection control device 3. Accordingly, the inspection control device 3 can appropriately detect the completion of the movement of the inspection device 4 based on the notification transmitted from the robot control device 2. The inspection control device 3 may detect the completion of the appearance inspection based on the notification from the robot control device 2.

When the robot control device 2 receives a repair welding execution command transmitted from the host device 1, the robot control device 2 controls the corresponding welding robot MC1 based on the repair welding execution command to execute a repair welding in accordance with a repair welding program generated by the inspection control device 3. When the robot control device 2 detects that the repair welding is completed, the robot control device 2 generates a repair welding completion report indicating that the repair welding is completed, and notifies the host device 1 of the repair welding completion report. Accordingly, the host device 1 can appropriately detect the completion of the repair welding based on the report transmitted from the robot control device 2. A method of detecting the completion of a repair welding by the robot control device 2 may be, for example, a method of determining the completion of a repair welding based on a signal indicating the completion of a repair welding from a sensor (not shown) provided in the wire feeding device 300, or may be a known method, and contents of the method of detecting the completion of a repair welding is not limited.

The welding robot MC1 serving as an example of a welding robot is connected to the robot control device 2 so that data can be communicated between the welding robot MC1 and the robot control device 2. The welding robot MC1 executes a main welding or a repair welding according to a command from the host device 1 under the control of the corresponding robot control device 2. As described above, the welding robot MC1 may include the main welding robot MC1a provided for a main welding and the repair welding robot MC1b provided for a repair welding. The inspection device 4 to be described later is attached to the welding robot MC1, and when the welding robot MC1 moves, the inspection device 4 also moves. Therefore, during an appearance inspection, the welding robot MC1 to which the inspection device 4 is attached moves under the control of the robot control device 2 based on the appearance inspection program execution command.

The inspection control device 3 serving as an example of a repair welding device is connected to the host device 1, the robot control device 2, and the inspection device 4 so that data can be communicated among the inspection control device 3, the host device 1, the robot control device 2, and the inspection device 4. When the inspection control device 3 receives the appearance inspection execution command transmitted from the host device 1, the inspection control device 3 executes an appearance inspection on a welded portion of a welded workpiece produced by the welding robot MC1 (for example, inspects whether a weld bead formed by a main welding conforms to a shape of a predetermined master bead) in cooperation with the inspection device 4, while the welding robot MC1 to which the inspection device 4 is attached moves under the control of the robot control device 2. For example, the inspection control device 3 controls the inspection device 4 to detect a shape of a weld bead formed in a welded portion based on welded portion information of a welded workpiece included in the appearance inspection execution command, and compares a shape of a predetermined weld master bead (not shown) for each main welding with a shape of an actually detected weld bead.

The inspection control device 3 generates an appearance inspection report based on the comparison, and transmits the appearance inspection report to the host device 1.

When the inspection control device 3 determines that an appearance inspection result of a welded workpiece is fail, the inspection control device 3 generates a repair welding program for correcting (repairing) a welding defective portion by using the appearance inspection result that indicates position information of a detected spot indicating a spot where a welding defective portion is detected and that is obtained from the inspection device 4. The inspection control device 3 transmits the repair welding program and the appearance inspection result to the robot control device 2 in association with each other. The inspection device 4 is connected to the inspection control device 3 so that data can be communicated between the inspection device 4 and the inspection control device 3. Although not shown in FIG. 1, when the inspection device 4 is attached to the welding robot MC1 (see FIG. 2), the inspection device 4 can be operated to three-dimensionally scan a mounting table on which a workpiece Wk is placed in accordance with driving of a manipulator 200 under the control of the robot control device 2. In order to inspect whether there is a welding defective portion in the workpiece Wk in accordance with the driving of the manipulator 200 under the control of the robot control device 2, the inspection device 4 acquires welded portion information included in the appearance inspection execution command transmitted from the inspection control device 3 and shape data of a weld bead of the welded portion based on the appearance inspection execution command, and transmits the welded portion information and the shape data of the weld bead of the welded portion to the inspection control device 3. The inspection control device 3 determines whether there is a welding defective portion in the welded portion (executes an appearance inspection) based on the shape data obtained from the inspection device 4 and shape data of the master bead described above. The inspection control device 3 generates, as an appearance inspection report, information about a defective portion (for example, a detected spot indicating a portion where a welding defect is detected, and a type of a welding defect) that is determined to be a welding defective portion among welded portions.

Figure 2:
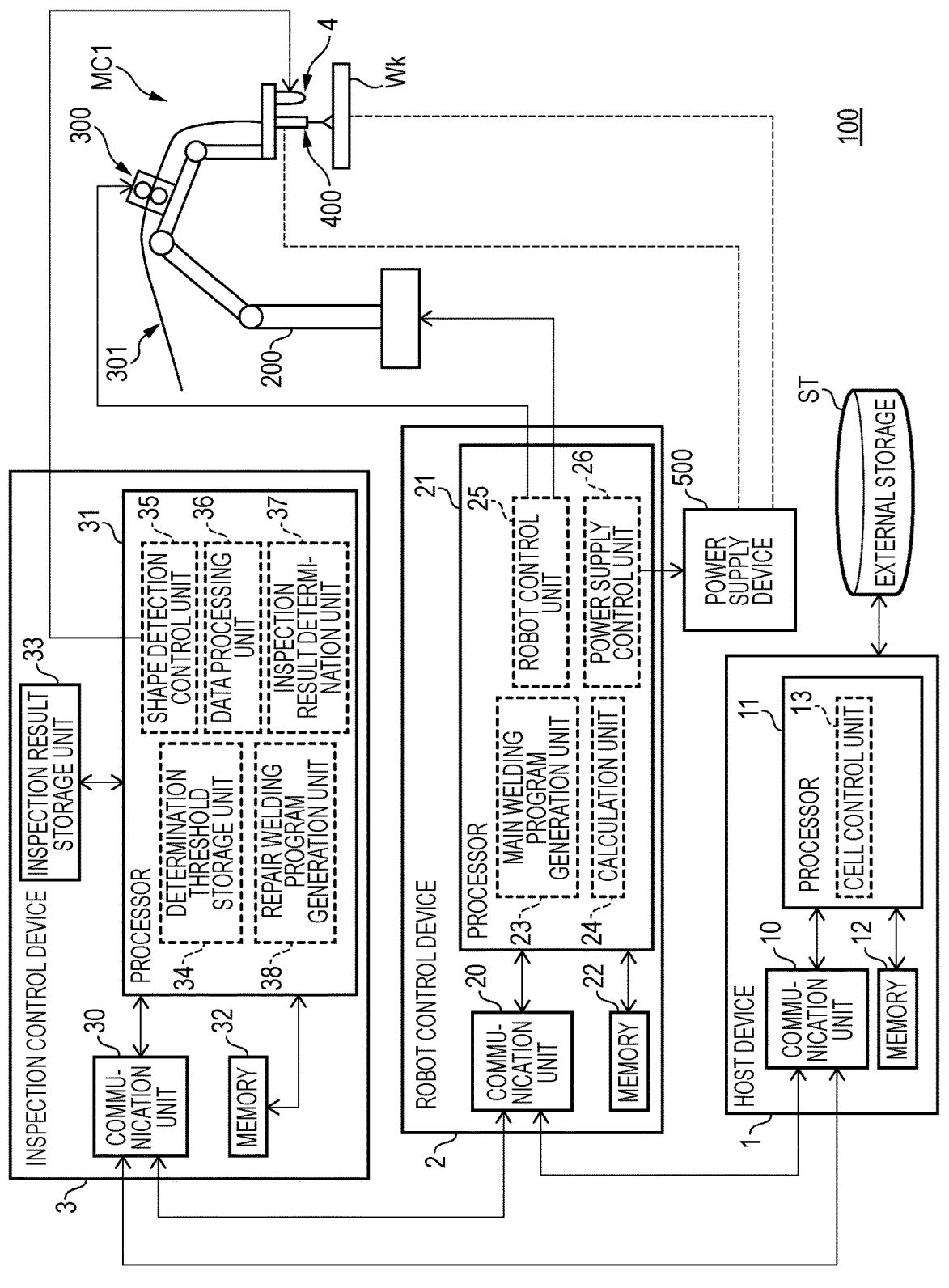
FIG. 2 is a diagram showing an internal configuration example of an inspection control device, a robot control device, and a host device according to a first embodiment.

FIG. 2 is a diagram showing an internal configuration example of the inspection control device 3, the robot control device 2, and the host device 1 according to the first embodiment. The monitor MN1 and the input interface UI1 are not shown in FIG. 2 in order to make the description easy to understand. Under the control of the robot control device 2, the welding robot MC1 executes various processes such as a main welding, a repair welding, and a movement of the inspection device 4 during an appearance inspection based on commands from the host device 1. The welding robot MC1 executes, for example, an arc welding in a process of a main welding or a repair welding. Alternatively, the welding robot MC1 may execute a welding (for example, a laser welding or a gas welding) other than the arc welding. In this case, although not shown, a laser head, instead of a welding torch 400, may be connected to a laser oscillator via an optical fiber. The welding robot MC1 includes at least the manipulator 200, the wire feeding device 300, a welding wire 301, and a welding torch 400.

The manipulator 200 includes an articulated arm, and moves each arm based on a control signal from a robot control unit 25 (see following description) of the robot control device 2. Accordingly, the manipulator 200 can change a positional relationship between the workpiece Wk and the welding torch 400 (for example, an angle of the welding torch 400 relative to the workpiece Wk) by driving the arm.

The wire feeding device 300 controls a feeding speed of the welding wire 301 based on a control signal (to be described later) from the robot control device 2. The wire feeding device 300 may include a sensor (not shown) that can detect a remaining amount of the welding wire 301. Based on an output of the sensor, the robot control device 2 can detect that a process of a main welding or a repair welding is completed.

The welding wire 301 is held by the welding torch 400. When power is supplied from a power supply device 500 to the welding torch 400, an arc is generated between a tip end of the welding wire 301 and the workpiece Wk, and an arc welding is executed. The illustration and description of a configuration and the like for supplying shielding gas to the welding torch 400 are omitted for the convenience of description.

The host device 1 generates an execution command of various processes of a main welding using a plurality of original workpieces or a repair welding in which a welding defective portion of a welded workpiece is corrected (repaired) by using welding related information input or set in advance by a user, and transmits the execution command to the robot control device 2. The host device 1 includes at least a communication unit 10, a processor 11, and a memory 12.

The communication unit 10 is connected to the robot control device 2 and the external storage ST so that data can be communicated among the communication unit 10, the robot control device 2, and the external storage ST. The communication unit 10 transmits an execution command of various processes of a main welding or a repair welding generated by the processor 11 to the robot control device 2. The communication unit 10 receives a main welding completion report, an appearance inspection report, and a repair welding completion report that are transmitted from the robot control device 2, and outputs the main welding completion report, the appearance inspection report, and the repair welding completion report to the processor 11. A main welding or repair welding execution command may include, for example, a control signal for controlling the manipulator 200, the wire feeding device 300, and the power supply device 500 included in the welding robot MC1.

The processor 11 is configured with, for example, a central processing unit (CPU) or a field programmable gate array (FPGA), and executes various processings and controls in cooperation with the memory 12. Specifically, the processor 11 implements functions of a cell control unit 13 by referring to a program stored in the memory 12 and executing the program.

The memory 12 includes, for example, a random access memory (RAM) serving as a work memory used when a processing of the processor 11 is executed, and a read only memory (ROM) that stores a program for defining a processing of the processor 11. The RAM temporarily stores data generated or acquired by the processor 11. A program that defines a processing of the processor 11 is written into the ROM. The memory 12 stores data of welding related information read from the external storage ST and data of workpiece information (see following description) that is related to a welded workpiece or a repaired and welded workpiece and is transmitted from the robot control device 2.

Based on the welding related information stored in the external storage ST, the cell control unit 13 generates an execution command that is used for executing a main welding using a plurality of original workpieces or executing a repair welding on a welded workpiece and that is defined (in other words, set) in the welding related information. Based on the welding related information stored in the external storage ST, the cell control unit 13 generates an appearance inspection program related to driving of the welding robot MC1 during an appearance inspection on a workpiece Wk (for example, a welded workpiece) after a main welding, and further generates an appearance inspection program execution command including the appearance inspection program. The appearance inspection program may be generated in advance and stored in the external storage ST. In this case, the cell control unit 13 simply reads and acquires the appearance inspection program from the external storage ST. The cell control unit 13 may generate different execution commands for various processes of a main welding or a repair welding to be executed by the welding robot MC1. The main welding or repair welding execution command generated by the cell control unit 13 or the appearance inspection program execution command including the appearance inspection program is transmitted to the corresponding robot control device 2 via the communication unit 10.

The robot control device 2 controls a processing of the corresponding welding robot MC1 (specifically, the manipulator 200, the wire feeding device 300, and the power supply device 500) based on a main welding or repair welding execution command transmitted from the host device 1. The robot control device 2 includes at least a communication unit 20, a processor 21, and a memory 22.

The communication unit 20 is connected to the host device 1, the inspection control device 3, and the welding robot MC1 so that data can be communicated among the communication unit 20, the host device 1, the inspection control device 3, and the welding robot MC1. Although illustration is simplified in FIG. 2, data is transmitted and received between the robot control unit 25 and the manipulator 200, between the robot control unit 25 and the wire feeding device 300, and between a power supply control unit 26 and the power supply device 500 via the communication unit 20. The communication unit 20 receives a main welding execution command, an appearance inspection program, or a repair welding execution command transmitted from the host device 1. The communication unit 20 transmits work-piece information of a welded workpiece produced by a main welding or workpiece information of a repaired and welded workpiece produced by a repair welding to the host device 1.

Here, the workpiece information not only includes an ID of a welded workpiece or a repaired and welded workpiece but also includes at least an ID of each of a plurality of original workpieces used in a main welding, a name, a welded portion, a welding condition at the time of executing a main welding, and a welding condition at the time of executing a repair welding.

Further, the workpiece information may include information (for example, coordinates) indicating a position of a detected spot indicating a defective portion of a welded workpiece. A welding condition or a repair welding condition includes, for example, a material and a thickness of an original workpiece, a material and a wire diameter of the welding wire 301, a type of shielding gas, a flow rate of the shielding gas, a set average value of a welding current, a set average value of a welding voltage, a feeding speed and a feeding amount of the welding wire 301, the number of times of welding, and welding time. In addition, the welding condition or the repair welding condition may include, for example, information indicating a type of a main welding or a repair welding (for example, a TIG welding, a MAG welding, or a pulse welding), and a moving speed and moving time of the manipulator 200.

The processor 21 is configured with, for example, a CPU or an FPGA, and executes various processings and controls in cooperation with the memory 22. Specifically, the processor 21 implements functions of a main welding program generation unit 23, a calculation unit 24, the robot control unit 25, and the power supply control unit 26 by referring to a program stored in the memory 22 and executing the program.

The memory 22 includes, for example, a RAM serving as a work memory used when a processing of the processor 21 is executed, and a ROM that stores a program for defining a processing of the processor 21. The RAM temporarily stores data generated or acquired by the processor 21. A program that defines a processing of the processor 21 is written into the ROM. The memory 22 stores data of a main welding execution command, an appearance inspection program, or a repair welding execution command transmitted from the host device 1, and data of workpiece information of a welded workpiece produced by a main welding or a repaired and welded workpiece produced by a repair welding. The memory 22 stores a main welding program or an appearance inspection program to be executed by the welding robot MC1. The main welding program is a program that defines a specific procedure (process) of a main welding in which a plurality of original workpieces are joined using a welding condition of the main welding. The appearance inspection program is a program that defines a movement in a movement range of the welding robot MC1 to which the inspection device 4 is attached during an appearance inspection (in other words, a range in which the entire workpiece Wk needs to be scanned to acquire shape data of the workpiece Wk to be subjected to an appearance inspection). Accordingly, the robot control device 2 can move the inspection device 4 so that the workpiece Wk can be scanned during an appearance inspection by executing the appearance inspection program.

The main welding program generation unit 23 uses work-piece information (for example, an ID, a name, and a welded portion of an original workpiece) of each of a plurality of original workpieces included in a main welding execution command transmitted from the host device 1 via the communication unit 20 to generate a main welding program for a main welding to be executed by the welding robot MC1 based on the main welding execution command. The main welding program may include various parameters such as a welding current, a welding voltage, an offset amount, a welding speed, and a posture of the welding torch 400 for controlling the power supply device 500, the manipulator 200, the wire feeding device 300, the welding torch 400, and the like during the execution of a main welding. The generated main welding program may be stored in the processor 21 or may be stored in the RAM of the memory 22.

The calculation unit 24 executes various calculations. For example, the calculation unit 24 calculates parameters for controlling the welding robot MC1 (specifically, the manipulator 200, the wire feeding device 300, and the power supply device 500) controlled by the robot control unit 25 based on the main welding program generated by the main welding program generation unit 23.

The robot control unit 25 generates a control signal for driving the welding robot MC1 (specifically, the manipulator 200, the wire feeding device 300, and the power supply device 500) based on the main welding program generated by the main welding program generation unit 23. The robot control unit 25 transmits the generated control signal to the welding robot MC1. The robot control unit 25 drives the manipulator 200 of the welding robot MC1 during an appearance inspection so as to inspect an operation range of the welding robot MC1 defined by the main welding program based on an appearance inspection program transmitted from the host device 1. As a result, the inspection device 4 (see FIG. 2) attached to the welding robot MC1 can move in accordance with the operation of the welding robot MC1, and can execute an appearance inspection on a welding defect in a weld bead of the workpiece Wk.

The power supply control unit 26 drives the power supply device 500 based on the main welding program generated by the main welding program generation unit 23 and a calculation result of the calculation unit 24.

The inspection control device 3 controls a processing of the appearance inspection on a welded workpiece produced by a main welding executed by the welding robot MC1 or a repaired and welded workpiece based on the appearance inspection execution command transmitted from the host device 1. The appearance inspection is, for example, to inspect whether a shape of a weld bead formed in a welded workpiece or a repaired and welded workpiece satisfies a predetermined welding standard or a strength standard of a welded portion, or satisfies a quality standard of the welded workpiece or the repaired and welded workpiece. In order to make the following description easy to understand, the inspection control device 3 executes an appearance inspection to inspect whether a weld bead formed in a workpiece Wk (for example, a welded workpiece or a repaired and welded workpiece) satisfies a predetermined welding standard (for example, the shape of the weld bead is the same as or similar to a shape of a predetermined master bead corresponding to the workpiece Wk) based on three dimension (3D) point cloud data indicating the shape of the weld bead acquired by the inspection device 4. Hereinafter, a welded portion determined to be greatly different from the shape of the master bead (that is, not the same as or similar to the shape of the master bead) in the 3D point cloud data indicating a shape of a weld bead is defined as a "detected spot". In other words, information indicating a position of the detected spot (for example, 3D position coordinates) is detected by the inspection control device 3. The inspection control device 3 includes at least a communication unit 30, a processor 31, a memory 32, and an inspection result storage unit 33.

The communication unit 30 is connected to the host device 1, the robot control device 2, and the inspection device 4 so that data can be communicated among the communication unit 30, the host device 1, the robot control device 2, and the inspection device 4. Although illustration is simplified in FIG. 2, data is transmitted and received between a shape detection control unit 35 and the inspection device 4 via the communication unit 30. The communication unit 30 receives an appearance inspection execution command transmitted from the host device 1. The communication unit 30 transmits a result of an appearance inspection (for example, whether there is a welding defective portion in a welded workpiece or a repaired and welded workpiece) executed by the inspection device 4 to the host device 1.

The processor 31 is configured with, for example, a CPU or an FPGA, and executes various processings and controls in cooperation with the memory 32. Specifically, the processor 31 implements functions of a determination threshold storage unit 34, the shape detection control unit 35, a data processing unit 36, an inspection result determination unit 37, and a repair welding program generation unit 38 by referring to a program stored in the memory 32 and executing the program.

The memory 32 includes, for example, a RAM serving as a work memory used when a processing of the processor 31 is executed, and a ROM that stores a program for defining a processing of the processor 31. The RAM temporarily stores data generated or acquired by the processor 31. A program that defines a processing of the processor 31 is written into the ROM. The memory 32 stores data of an appearance inspection execution command of a welded workpiece transmitted from the host device 1, and data of workpiece information of a welded workpiece produced by a main welding or a repaired and welded workpiece produced by a repair welding. The memory 32 also stores data of a repair welding program generated by the repair welding program generation unit 38. The repair welding program is a program that defines a specific procedure (process) of a repair welding in which a welding defective portion in a welded workpiece is corrected (repaired) by using a welding condition of the repair welding and position information of a corresponding portion (corresponding spot) on an operation trajectory of the welding robot MC1 that is closest to a detected spot. The repair welding program is generated by the repair welding program generation unit 38 and is transmitted from the inspection control device 3 to the robot control device 2.

The inspection result storage unit 33 is configured with, for example, a hard disk or a solid state drive. The inspection result storage unit 33 stores data indicating an appearance inspection result of a welded portion of a workpiece Wk (for example, a welded workpiece or a repaired and welded workpiece) as an example of data generated or acquired by the processor 31. The data indicating an appearance inspection result is generated by, for example, the inspection result determination unit 37.

The determination threshold storage unit 34 is configured with, for example, a cache memory provided in the processor 31, and stores a threshold (for example, a threshold set corresponding to a welded portion) used in a determination processing to be executed by the inspection result determination unit 37 corresponding to the welded portion. Examples of the threshold include an allowable range (threshold) related to a positional deviation of a welded portion, a threshold related to a height of a weld bead, and a threshold related to a width of a weld bead. The determination threshold storage unit 34 may store an allowable range that satisfies a minimum welding quality required by a customer or the like (for example, a minimum allowable value, a maximum allowable value, or the like related to a height of a weld bead) as the threshold during an appearance inspection after a repair welding. Further, the determination threshold storage unit 34 may store an upper limit of the number of times of appearance inspections for each welded portion. Accordingly, in a case where the number of times of appearance inspections exceeds a predetermined upper limit of the number of times when a defective portion is corrected by a repair welding, the inspection control device 3 determines that it is difficult or it is less likely to correct the defective portion by an automatic repair welding executed by the welding robot MC1, and can prevent a decrease in an operation rate of the welding system 100.

Based on an appearance inspection execution command of a welded portion of a workpiece Wk (for example, a welded workpiece) transmitted from the host device 1 or the robot control device 2, the shape detection control unit 35 acquires shape data (for example, 3D point cloud data) that is related to a weld bead in a welded portion and is transmitted from the inspection device 4 while the robot control device 2 operates the welding robot MC1 to which the inspection device 4 is attached based on the appearance inspection program during an appearance inspection. When the inspection device 4 is positioned at a position where the inspection device 4 can image a welded portion (in other words, a three-dimensional shape of the welded portion can be detected) in accordance with the driving of the manipulator 200 by the robot control device 2 as described above, the shape detection control unit 35 causes the inspection device 4 to emit, for example, a laser beam to acquire shape data of a weld bead in the welded portion. When the shape detection control unit 35 receives the shape data of the weld bead acquired by the inspection device 4, the shape detection control unit 35 transmits the shape data to the data processing unit 36.

The data processing unit 36 converts the shape data of the weld bead in the welded portion transmitted from the shape detection control unit 35 into image data indicating a three-dimensional shape of the welded portion. The shape data is, for example, point cloud data of shape lines including a reflection trajectory of a laser beam emitted onto a surface of the weld bead. The data processing unit 36 executes a statistical processing on the input shape data, and generates image data related to the three-dimensional shape of the weld bead in the welded portion. In order to emphasize a position and a shape of the weld bead, the data processing unit 36 may execute an edge emphasis correction in which a peripheral edge portion of the weld bead is emphasized. The data processing unit 36 may count the number of times of appearance inspections for each welded portion or defective portion, and determine that it is difficult or it is less likely to correct the defective portion by an automatic repair welding when the number of times of appearance inspections exceeds the number of times stored in advance in the memory 32 and when a welding inspection result is not good. In this case, the inspection result determination unit 37 generates an alert screen including a position of the defective portion and a defect factor, and transmits the generated alert screen to the host device 1 via the communication unit 30. The alert screen transmitted to the host device 1 is displayed on the monitor MN1.

The inspection result determination unit 37 uses the threshold stored in the determination threshold storage unit 34 to determine whether a welded portion satisfies a predetermined welding standard (for example, whether a shape of a weld bead formed by a main welding or a repair welding is the same as or is similar to a shape of a corresponding master bead) based on shape data that is related to a weld bead in a welded portion and is acquired by the shape detection control unit 35. The inspection result determination unit 37 measures a position of a detected spot of a welding defect (for example, a start position and an end position of a defective portion (see FIG. 4), a position of a hole formed in a weld bead, a position of an undercut, and the like), and analyzes defect contents to estimate a defect factor. In the determination described above, the inspection result determination unit 37 calculates an inspection score for each welded portion on a welding line formed on a weld bead based on shape data of the weld bead. The inspection result determination unit 37 serving as an example of an inspection result acquisition unit generates and acquires the measured position of the defective portion, the inspection score, and the estimated defect factor as an appearance inspection result (an appearance inspection report) for a welded portion, stores the generated appearance inspection result in the memory 32, and transmits the appearance inspection result to the host device 1 via the communication unit 30. The inspection result determination unit 37 may determine whether a repair welding can be executed by the welding robot MC1 (in other words, whether it is better to execute a repair welding by the welding robot MC1 or by hand) based on the inspection score described above, and may include a determination result in the appearance inspection result (the appearance inspection report) and output the appearance inspection result.

The repair welding program generation unit 38 generates a repair welding program for a workpiece Wk (for example, a welded workpiece or a repaired and welded workpiece) to be executed by the welding robot MC1 by using the appearance inspection result of the workpiece Wk (for example, a welded workpiece or a repaired and welded workpiece) output from the inspection result determination unit 37 and workpiece information of a welded workpiece or a repaired and welded workpiece (for example, information such as coordinates indicating a position of a detected spot of a welding defect of a welded workpiece or a repaired and welded workpiece). The details of a procedure for creating the repair welding program will be described later with reference to FIGS. 4, 5, and 6. The repair welding program may include various parameters such as a welding current, a welding voltage, an offset amount, a welding speed, and a posture of the welding torch 400 for controlling the power supply device 500, the manipulator 200, the wire feeding device 300, the welding torch 400, and the like during the execution of a repair welding. The generated repair welding program may be stored in the processor 31 or in the RAM of the memory 32.

The inspection device 4 is, for example, a three-dimensional shape sensor, and is attached to a tip end of the welding robot MC1. The inspection device 4 can acquire a plurality of pieces of point cloud data capable of specifying a shape of a welded portion of a workpiece Wk (for example, a welded workpiece), and generates shape data of the welded portion (in other words, image data of a weld bead) based on the point group data and transmits the shape data to the inspection control device 3. When the inspection device 4 is not attached to the tip end of the welding robot MC1 and is disposed separately from the welding robot MC1, the inspection device 4 may include a laser light source (not shown) that can scan a welded portion of a workpiece Wk (for example, a welded workpiece or a repaired and welded workpiece) based on welded portion position information transmitted from the inspection control device 3, and a camera (not shown) that is disposed in a manner of capable of imaging an imaging region including a periphery of the welded portion and that images a reflection trajectory (that is, shape lines of the welded portion) of reflected laser light among laser light emitted onto the welded portion. In this case, the inspection device 4 transmits shape data (in other words, image data of a weld bead) of the welded portion based on laser light captured by the camera to the inspection control device 3. The camera described above includes at least a lens (not shown) and an image sensor (not shown). The image sensor is, for example, a solid-state imaging element such as a charge coupled device (CCD) or a complementary metal oxide semiconductor (CMOS), and converts an optical image formed on an imaging surface into an electric signal.

(Operation of Welding System)

Figure 3A:
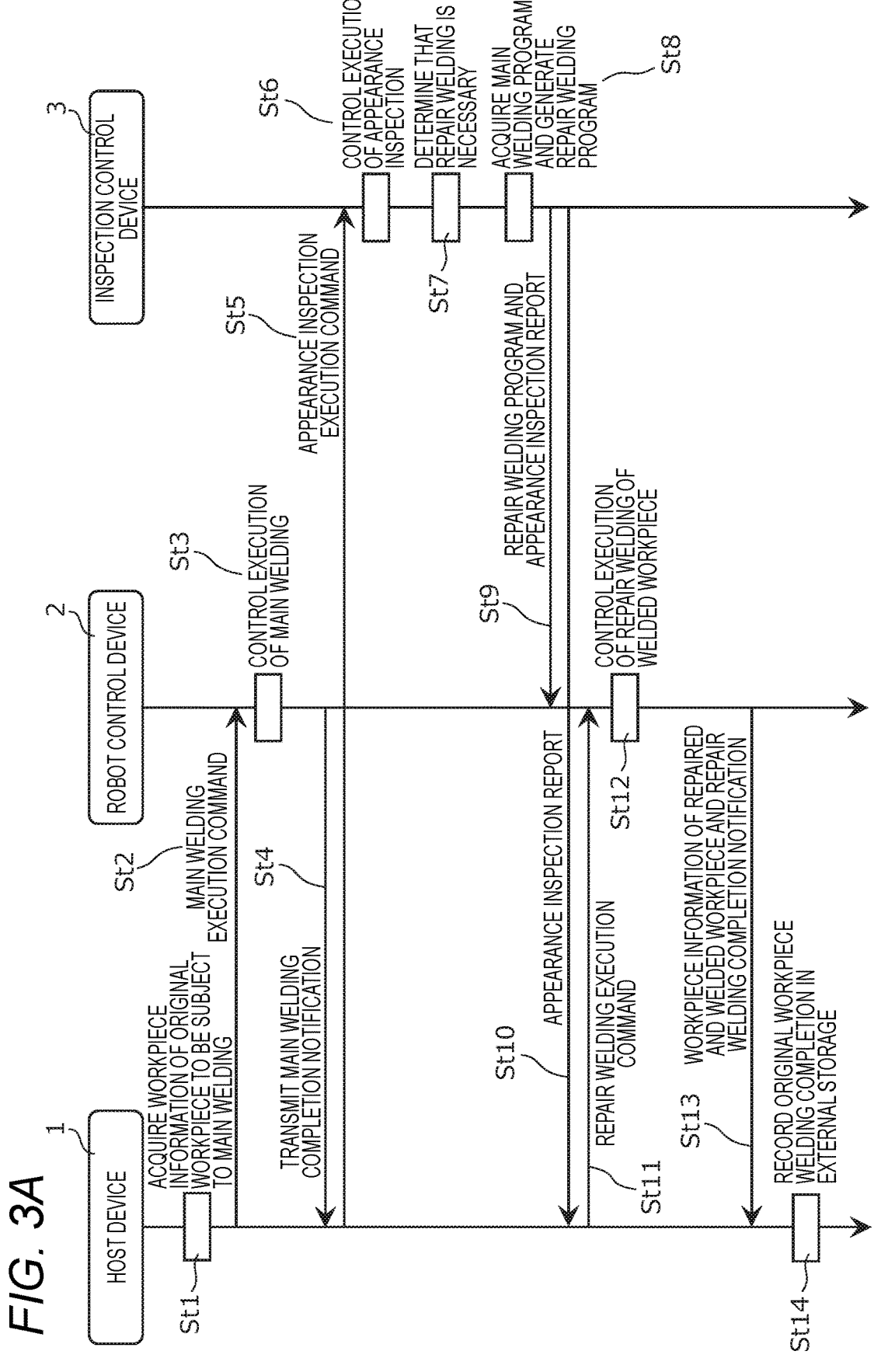
FIG. 3A is a sequence diagram showing an example of an operation procedure of a main welding and a repair welding that are executed by a welding system according to the first embodiment.
Figure 3B:
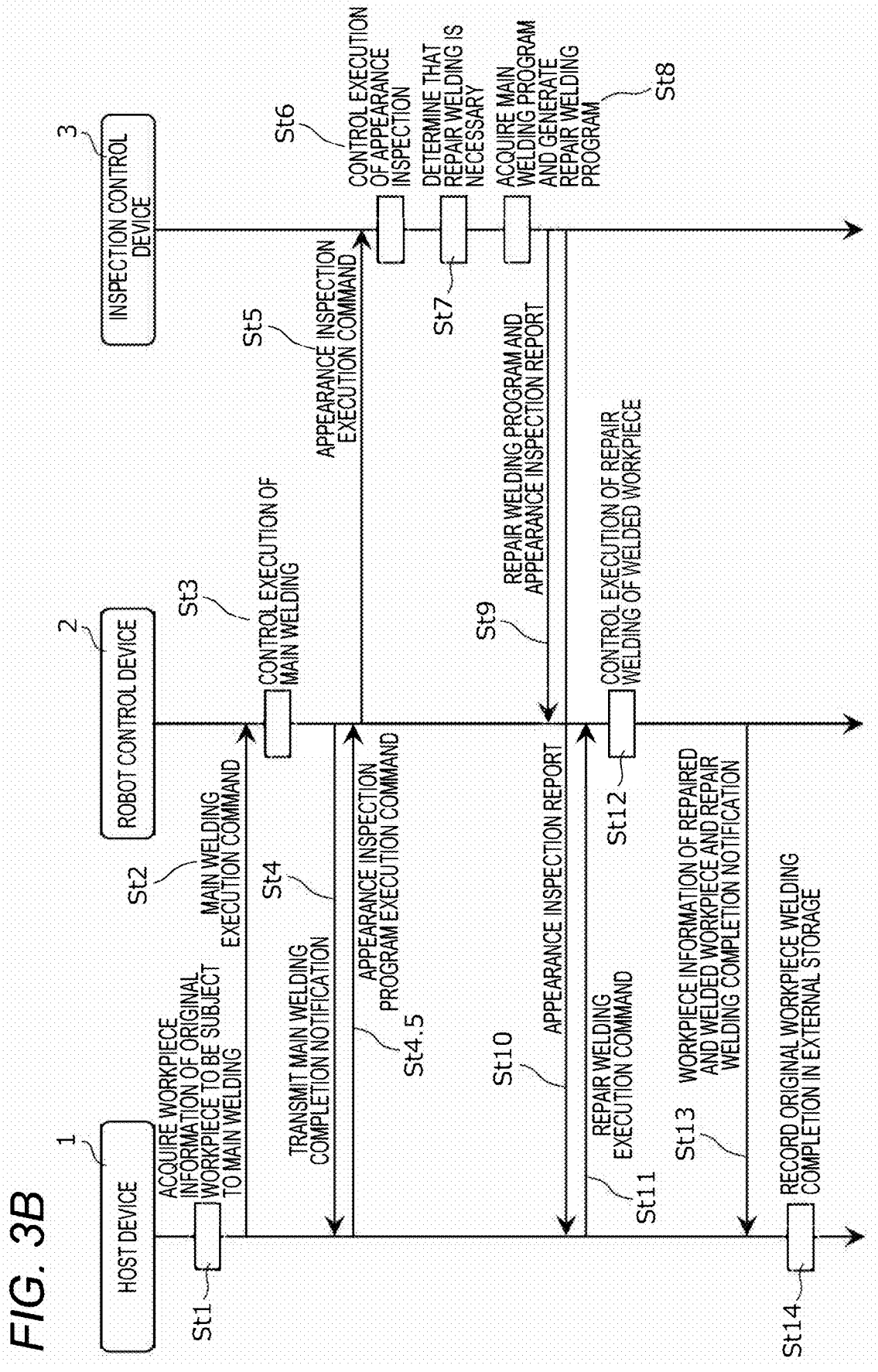
FIG. 3B is a sequence diagram showing a modification of the operation procedure of the main welding and the repair welding that are executed by the welding system according to the first embodiment.

Next, an operation procedure of a main welding and a repair welding that are executed by the welding system 100 according to the first embodiment will be described with reference to FIG. 3A. FIG. 3A is a sequence diagram showing an example of an operation procedure of a main welding and a repair welding that are executed by the welding system 100 according to the first embodiment. FIG. 3B is a sequence diagram showing a modification of the operation procedure of the main welding and the repair welding that are executed by the welding system 100 according to the first embodiment. In the description of FIGS. 3A and 3B, an operation procedure executed among the host device 1, the robot control device 2, and the inspection control device 3 for each process of a main welding using a plurality of original workpieces and a repair welding executed based on a fact that an appearance inspection result of a welded workpiece is fail will be described as an example.

In FIG. 3A or FIG. 3B, the host device 1 acquires workpiece information of an original workpiece (for example, an ID, a name, and a welded portion of an original workpiece) to be subjected to a main welding (St1), and generates a main welding execution command including the workpiece information of the original workpiece. The host device 1 transmits the main welding execution command including the workpiece information of the original workpiece to the robot control device 2 (St2). The robot control device 2 may execute the processings of step St1 and step St2 without going through the host device 1. In this case, it is preferable that data the same as data stored in the external storage ST is stored in the memory 22 of the robot control unit 2, or the robot control unit 2 is connected to the external storage ST so that the robot control device 2 can acquire data from the external storage ST.

When the robot control device 2 receives the main welding execution command transmitted from the host device 1, the robot control device 2 uses workpiece information of a plurality of original workpieces included in the main welding execution command to generate a main welding program for a main welding to be executed by the welding robot MC1, and causes the welding robot MC1 to execute the main welding in accordance with the main welding program (St3). When the robot control device 2 determines that the main welding executed by the welding robot MC1 is completed using various known methods, the robot control device 2 generates a main welding completion notification indicating that the main welding is completed and transmits the notification to the host device 1 (St4). When the host device 1 receives the main welding completion notification, the host device 1 generates an appearance inspection execution command for a welded workpiece, and transmits the appearance inspection execution command to the inspection control device 3 (St5). As shown in FIG. 3B, when the host device 1 receives the main welding completion notification, the host device 1 may generate an appearance inspection program execution command including an appearance inspection program of a welded workpiece and transmit the appearance inspection program execution command to the robot control device 2 (St4.5). In this case, as shown in FIG. 3B, the robot control device 2 generates an appearance inspection execution command of the welded workpiece and transmits the appearance inspection execution command to the inspection control device 3 (St5), executes the appearance inspection program received from the host device 1 accompanying with the start of the appearance inspection, and moves the inspection device 4 attached to the welding robot MC1.

While the inspection device 4 is moved by the robot control device 2 so as to be able to scan a welded portion of the welded workpiece, the inspection control device 3 causes the inspection device 4 to execute an appearance inspection on the welded workpiece based on the appearance inspection execution command transmitted in step St5 (St6). As a result of the appearance inspection in step St6, the inspection control device 3 determines that a repair welding is necessary because there is a welding defective portion in the welded workpiece (St7), acquires the main welding program from the robot control device 2 (St8), and generates a repair welding program by modifying a part of the main welding program (St8). The modified part is, for example, contents indicating a portion (range) where a repair welding is to be executed.

Although not shown in details in FIGS. 3A and 3B, the inspection control device 3 may request data of the main welding program from the robot control device 2 in step St8 and acquire the data of the main welding program transmitted from the robot control device 2 in response to the request, or may acquire the data of the main welding program transmitted from the robot control device 2 after the step St3 in advance. Accordingly, the inspection control device 3 can efficiently generate data of the repair welding program by partially modifying the acquired data of the main welding program. The inspection control device 3 generates an appearance inspection report including a determination result in step St7 and the repair welding program, and transmits the appearance inspection report to the robot control device 2 (St9). The inspection control device 3 transmits the appearance inspection report generated in the same manner to the host device 1 (St10).

When the host device 1 receives the appearance inspection report in step St10, the host device 1 generates a repair welding execution command for a welded workpiece, and transmits the repair welding execution command to the robot control device 2 (St11). When the robot control device 2 receives the repair welding execution command transmitted from the host device 1, the robot control device 2 causes the welding robot MC1 to execute a repair welding in accordance with the repair welding program based on the repair welding program (received in step St9) for the welded workpiece designated by the repair welding execution command (St12). When the robot control device 2 determines that the repair welding executed by the welding robot MC1 is completed using various known methods, the robot control device 2 transmits workpiece information of a repaired and welded workpiece (for example, an ID of a repaired and welded workpiece W4, workpiece information including respective IDs of a plurality of original workpieces used in a main welding (for example, an ID of an original workpiece, a name, a welded portion of an original workpiece, and welding conditions at the time of executing the main welding and the repair welding)) to the host device 1 (St13).

When the host device 1 receives the workpiece information including the ID of the repaired and welded workpiece transmitted from the robot control device 2, the host device 1 sets a management ID suitable for a user business operator corresponding to the ID of the repaired and welded workpiece, and stores data indicating that welding for the repaired and welded workpiece corresponding to the management ID is completed in the external storage ST (St14).

Next, an operation outline example for specifying a repaired and welded portion by using a detected spot (that is, a position indicating a welding defective portion) output from the inspection device 4 in the generation of the repair welding program will be described in detail with reference to FIGS. 4, 5, and 6.

(First Operation Outline Example)

Figure 4:
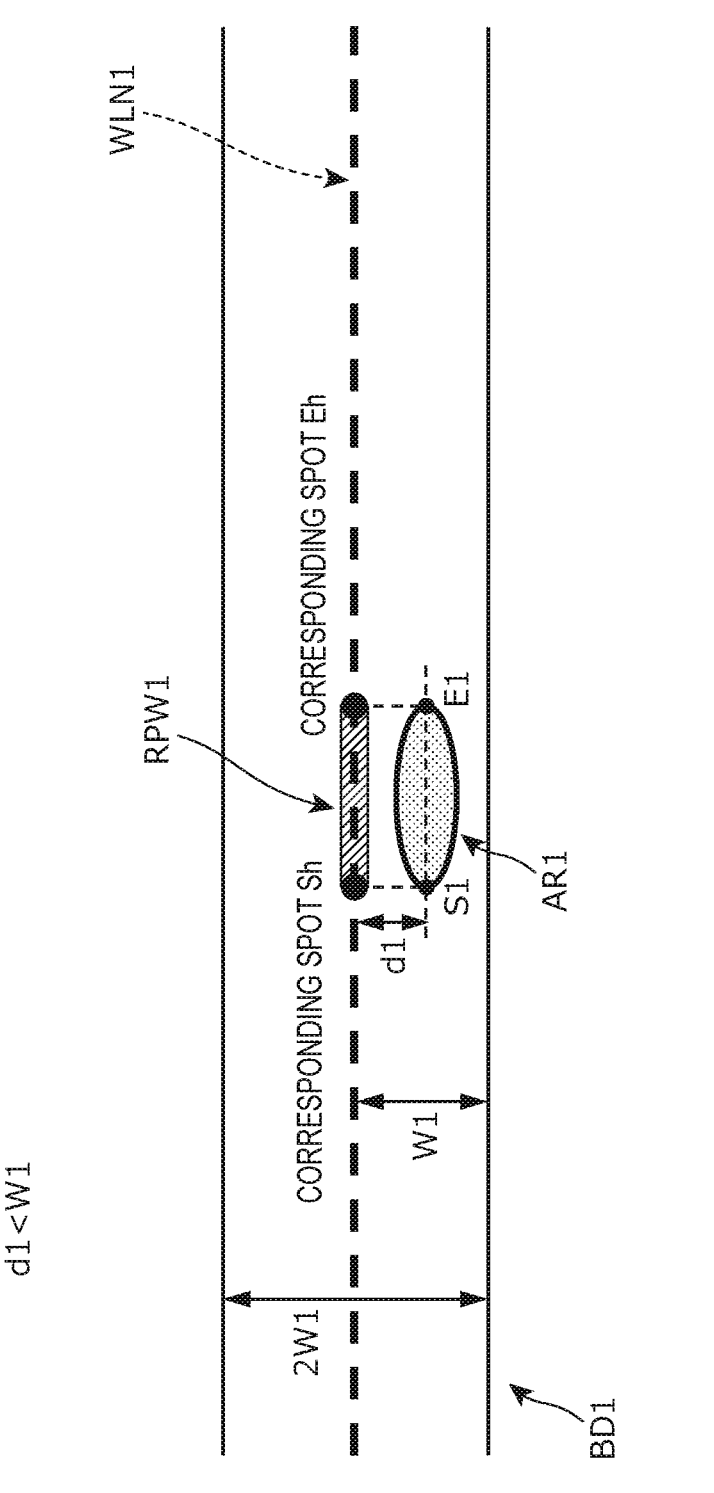
FIG. 4 is a diagram schematically showing a first operation outline example related to specification of a repaired and welded portion corresponding to a detected spot region obtained by an appearance inspection.

FIG. 4 is a diagram schematically showing a first operation outline example related to specification of a repaired and welded portion corresponding to a detected spot region AR1 obtained by an appearance inspection. FIG. 6 is a flowchart showing an example of an operation procedure related to the generation of a repair welding program. In the first embodiment, processings in the flowchart shown in FIG. 6 are executed by the processor 31 (specifically, the repair welding program generation unit 38) incorporated in the inspection control device 3.

In the first operation outline example, it is assumed that the detected spot region AR1 in which a defective portion of a weld bead BD1 is detected is created within a half width equivalent length W1 of the weld bead BD1 from a welding line WLN1 (d1<W1). d1 indicates a distance of the detected spot region AR1 from the welding line WLN1. Here, in order to simplify the description, it is assumed that both a start detected spot S1 and an end detected spot E1 are located at the same distance from the welding line WLN1, and the detected spot region AR1 is located at substantially the same distance from the welding line WLN1.

The detected spot region AR1 indicates a range in which a welding defective portion occurs in an appearance inspection, and indicates, for example, a region from the start detected spot S1 to the end detected spot E1 in FIG. 4. Although the detected spot region AR1 has an elliptical shape in FIG. 4, a shape of the detected spot region AR1 is not limited to an elliptical shape. In order to make the description of FIGS. 4 and 5 easy to understand, a shape of the welding lines WLN1 and WLN2 is shown as a linear shape, but the shape of the welding lines WLN1 and WLN2 is not limited to a linear shape, and may have, for example, an arc shape, a combination of a linear shape and an arc shape, or a general shape including an arc shape.

Figure 6:
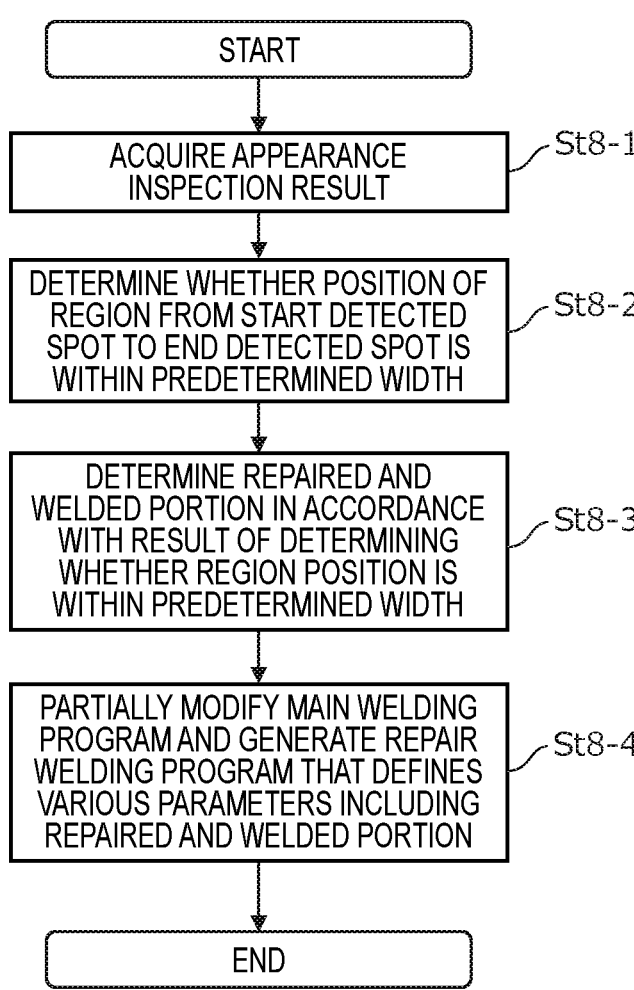
FIG. 6 is a flowchart showing an example of an operation procedure related to generation of a repair welding program.

In FIG. 6, the repair welding program generation unit 38 acquires an appearance inspection result generated by the inspection result determination unit 37 (St8-1). The repair welding program generation unit 38 uses the appearance inspection result acquired in step St8-1 to determine whether a position of the detected spot region AR1 (for example, a region from the start detected spot S1 to the end detected spot E1 shown in FIG. 4) included in the appearance inspection result is within a predetermined width (see following description) from the welding line WLN1 (St8-2). The repair welding program generation unit 38 determines a repaired and welded portion according to the determination result in step St8-2 (that is, a determination result of determining whether the position of the detected spot region AR1 is within the predetermined width from the welding line WLN1) (St8-3). The repair welding program generation unit 38 refers to the main welding program, and generates a repair welding program in which the repaired and welded portion determined in step St8-3 and various parameters (for example, a welding condition) used in a repair welding are partially modified from contents of the main welding program (St8-4).

In FIG. 4, the weld bead BD1 is formed by an operation trajectory of the welding robot MC1 during a main welding. The welding line WLN1 indicates an operation trajectory of the welding robot MC1 defined in the main welding program. A welding defect such as a bead crack is detected in the detected spot region AR1 due to a welding defect of the welding robot MC1 during a main welding, and the inspection control device 3 acquires data (for example, coordinates) indicating the position of the detected spot region AR1 that is a region from the start detected spot S1 to the end detected spot E1.

As shown in FIG. 4, when it is detected that the detected spot region AR1 is located at a position where the distance d1 of the detected spot region AR1 from the welding line WLN1 is within a predetermined width (for example, the half width equivalent length W1 of the weld bead BD1) (in other words, at a position close to the welding line WLN1), it is considered in a repair welding that an operation of the welding robot MC1 is more efficient when the welding robot MC1 limitedly executes the repair welding on a corresponding position on the welding line WLN1 in the same manner as the main welding program. In a case where the detected spot region AR1 is present in a manner of crossing a position (that is, one end portion of the weld bead BD1) separated from the welding line WLN1 by a distance of a predetermined width (for example, the half width equivalent length W1) (in other words, in a case where a position of either the start detected spot S1 or the end detected spot E1 of the detected spot region AR1 is outside the weld bead BD1), it is considered that the detected spot region AR1 exceeds the predetermined width (see above description). In this case, the repair welding program generation unit 38 determines and sets a repair welding section in accordance with an example in FIG. 5 to be described later.

The half width equivalent length W1 indicates a length substantially equivalent to a half of a width of the weld bead BD1 (=2×W1). The predetermined width is not limited to the half width equivalent length W1 of the weld bead BD1, and may be a designated length designated by a user based on the width of the weld bead (that is, a weld bead assumed in advance) defined in the main welding program before the main welding is started, and the same applies hereinafter. The designated length may be the same as or different from the half width equivalent length W1. The half width equivalent length W1 indicating the predetermined width may be set to any value in consideration of a risk of interference with a surrounding jig or the like by a user.

Therefore, the repair welding program generation unit 38 determines and sets a section of a foot of a perpendicular line drawn from each of the start detected spot S1 and the end detected spot E1 down to the welding line WLN1 (that is, a section from a start corresponding point Sh to an end corresponding point Eh) as a repair welding section RPW1. Accordingly, since a position where the detected spot region AR1 is detected is close to the welding line WLN1 (see FIG. 4), the repair welding program generation unit 38 can set a part of an operation trajectory of the welding robot MC1 as a repair welding section, and thus the repair welding program generation unit 38 can generate a repair welding program capable of executing a repair welding while efficiently moving the welding robot MC1 in the same manner as in a main welding.

(Second Operation Outline Example)

Figure 5:
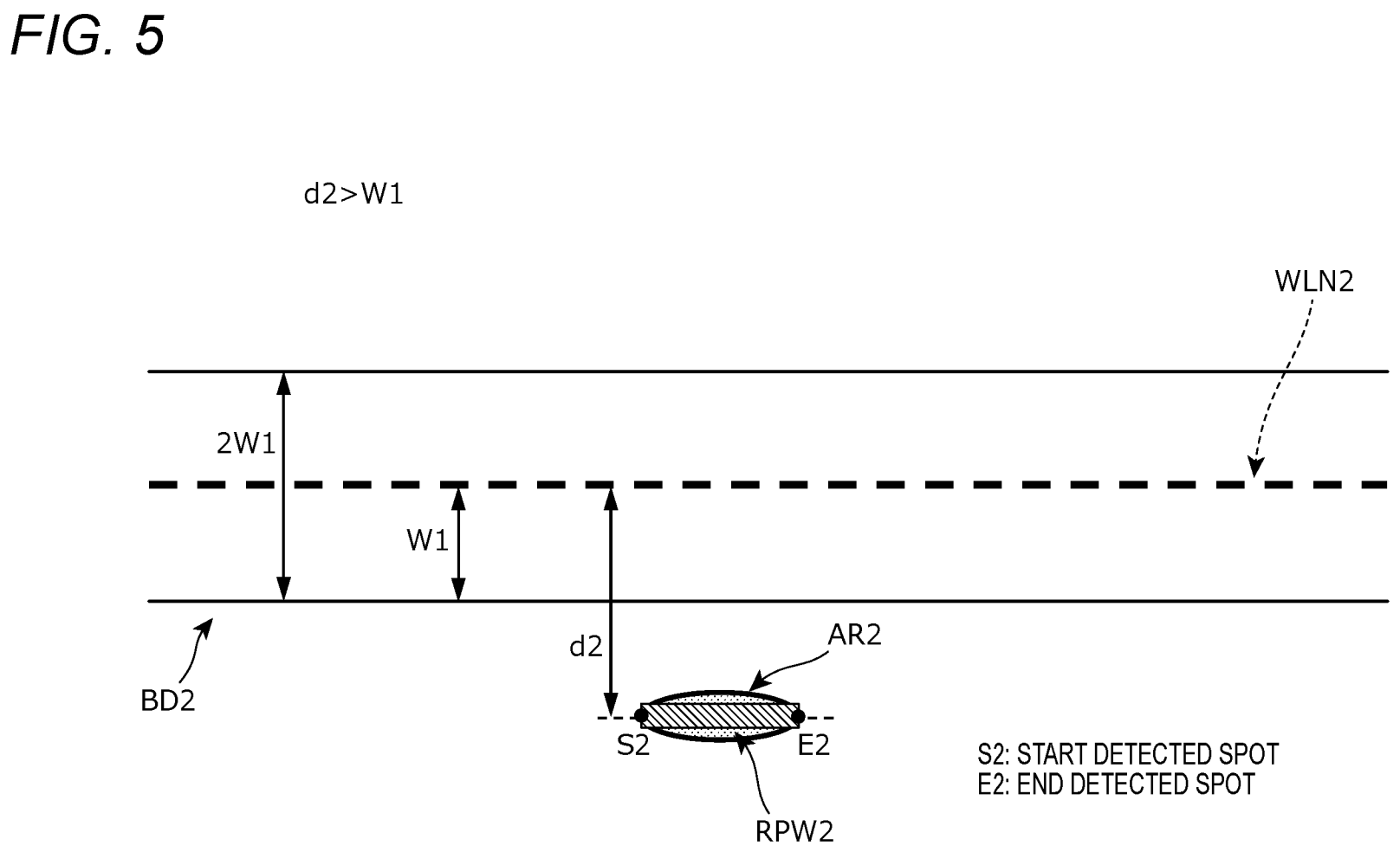

FIG. 5 is a diagram schematically showing a second operation outline example related to the specification of a repaired and welded portion corresponding to a detected spot region AR2 obtained by an appearance inspection. FIG. 6 is a flowchart showing an example of an operation procedure related to the generation of a repair welding program. In the first embodiment, processings in the flowchart shown in FIG. 6 are executed by the processor 31 (specifically, the repair welding program generation unit 38) incorporated in the inspection control device 3.

In the second operation outline example, it is assumed that the detected spot region AR2 in which a defective portion of a weld bead BD2 is detected is located outside a welding line WLN2 in a manner of exceeding a half width equivalent length W1 of the weld bead BD2 (d2>W1). d2 indicates a distance of the detected spot region AR2 from the welding line WLN2. Here, in order to simplify the description, it is assumed that both a start detected spot S2 and an end detected spot E2 are located at the same distance from the welding line WLN2, and the detected spot region AR2 is located at substantially the same distance from the welding line WLN2. The detected spot region AR2 indicates a range in which a welding defective portion occurs in an appearance inspection, and indicates, for example, a region from the start detected spot S2 to the end detected spot E2 in FIG. 5. Although the detected spot region AR2 has an elliptical shape in FIG. 5, a shape of the detected spot region AR2 is not limited to an elliptical shape. In the second operation outline example, description of contents the same as the description of FIG. 6 will be simplified or omitted, and different contents will be described.

In FIG. 6, the repair welding program generation unit 38 uses the appearance inspection result acquired in step St8-1 to determine whether a position of the detected spot region AR2 (for example, a region from the start detected spot S2 to the end detected spot E2 shown in FIG. 5) included in the appearance inspection result is within a predetermined width (see above description) from the welding line WLN2 (St8-2). The repair welding program generation unit 38 determines a repaired and welded portion according to the determination result in step St8-2 (that is, a determination result of determining whether the position of the detected spot region AR2 is within the predetermined width from the welding line WLN2) (St8-3). The repair welding program generation unit 38 refers to the main welding program, and generates a repair welding program in which the repaired and welded portion determined in step St8-3 and various parameters (for example, a welding condition) used in a repair welding are partially modified from contents of the main welding program (St8-4).

In FIG. 5, the weld bead BD2 is formed by an operation trajectory of the welding robot MC1 during a main welding. The welding line WLN2 indicates an operation trajectory of the welding robot MC2 defined in the main welding program. A welding defect such as a bead crack is detected in the detected spot region AR2 due to a welding defect of the welding robot MC2 during a main welding, and the inspection control device 3 acquires data (for example, coordinates) indicating the position of the detected spot region AR2 that is a region from the start detected spot S2 to the end detected spot E2.

As shown in FIG. 5, when it is detected that the detected spot region AR2 is outside the welding line WLN2 (in other words, at a position far from the welding line WLN2) and the distance d2 of the detected spot region AR2 from the welding line WLN2 exceeds a predetermined width (for example, the half width equivalent length W1 of the weld bead BD2), different from the main welding program, it is considered in a repair welding that a direct repair welding on the detected spot region AR2 by the welding robot MC1 is more efficient in repairing a welding defect of the detected spot region AR2 with high accuracy although there is a risk of interference between the welding robot MC1 and a jig, a welded workpiece, or another robot (not shown). The half width equivalent length W1 indicates a length substantially equivalent to a half of a width of the weld bead BD2 (=2×W1). Therefore, the repair welding program generation unit 38 determines and sets the detected spot region AR2 from the start detected spot S2 to the end detected spot E2 as a repair welding section RPW2. Accordingly, since a position where the detected spot region AR2 is detected is farther from the welding line WLN2 than the predetermined width (see FIG. 5), the repair welding program generation unit 38 can directly modify a part of the operation trajectory of the welding robot MC1 to the position of the detected spot region AR2 and set a repair welding section, and can generate a repair welding program capable of executing a repair welding in which directly repairing of the detected spot region AR2 is prioritized over a movement on the operation trajectory of the welding robot MC1.

As described above, in the welding system 100 according to the first embodiment, the repair welding device (for example, the inspection result determination unit 37) acquires an appearance inspection result including information about a position of a defective portion (for example, the detected spot region AR1) of a weld bead of a welded workpiece produced by a main welding that is executed by the welding robot MC1. The repair welding device (for example, the robot control unit 25) instructs the welding robot MC1 to execute a repair welding on the position of the defective portion by using the appearance inspection result based on a relationship between the position of the defective portion and a predetermined width (for example, see FIG. 4 or FIG. 5) related to the weld bead.

As a result, the repair welding device can automatically and more efficiently executes a repair welding on a defective portion of a welded workpiece produced by a main welding. That is, during a repair welding, the repair welding device can partially modify a part (for example, a section to be repaired and welded) of the main welding program during a main welding and sets a repair welding section in accordance with a positional relationship between the defective portion and the weld bead, and can adaptively execute a repair welding on the defective portion in accordance with the position of the defective portion.

The repair welding device generates a repair welding program for executing a repair welding on the position of the defective portion by using the appearance inspection result. The repair welding device causes the welding robot MC1 to execute the repair welding on the defective portion in accordance with the generated repair welding program. Accordingly, the repair welding device can generate a repair welding program in which a repair welding section is set while improving operation efficiency of the welding robot MC1 based on a positional relationship between a detected spot region (for example, see FIG. 4 or FIG. 5) obtained in an appearance inspection and the weld bead, and can execute, with high accuracy, the repair welding in which repairing of a defective portion is prioritized based on the repair welding program.

The predetermined width is, for example, the half width equivalent length W1 of the weld bead. When a defective portion (for example, the detected spot region AR1) is located within the half width equivalent length W1 from the welding line WLN1 (see FIG. 4), the repair welding device sets, as the repair welding section RPW1, a section from the start corresponding point Sh on the operation trajectory of the welding robot MC1 during a main welding corresponding to a start point (the start detected spot S1) of a defective portion region (the detected spot region AR1) included in an appearance inspection result to the end corresponding point Eh on the operation trajectory of the welding robot MC1 during the main welding corresponding to an end point (the end detected spot E1) of the defective portion region (the detected spot region AR1) included in the appearance inspection result. As a result, since a position where the detected spot region AR1 is detected is close to the welding line WLN1, the repair welding device can set a part of the operation trajectory of the welding robot MC1 as the repair welding section RPW1, and can execute a repair welding with high accuracy while efficiently moving the welding robot MC1 in the same manner as in a main welding. For example, during a repair welding, the repair welding device can prevent interference with a welded workpiece to be repaired and welded or a jig for fixing the welded workpiece, and thus can efficiently support smooth driving of the welding robot MC1.

The predetermined width is, for example, a half width equivalent length W1 of a weld bead. When a defective portion (for example, the detected spot region AR2) is located outside the welding line WLN2 in a manner of exceeding the half width equivalent length W1, the repair welding device sets, as the repair welding section RPW2, a section from a start point (the start detected spot S2) of a defective portion region (the detected spot region AR2) included in an appearance inspection result to an end point (the end detected spot E2) of the defective portion region (the detected spot region AR2) included in the appearance inspection result. Accordingly, since a position where the detected spot region AR2 is detected is farther from the welding line WLN2 than the predetermined width (see FIG. 5), the repair welding device can directly modify a part of the operation trajectory of the welding robot MC1 to a position of the detected spot region AR2 and set a repair welding section, and can appropriately execute a repair welding in which directly repairing of the detected spot region AR2 is prioritized over a movement on the operation trajectory of the welding robot MC1. For example, during a repair welding, although there is a risk of interference with a welded workpiece to be repaired and welded or a jig for fixing the welded workpiece, the repair welding device can improve a completion degree of a repaired and welded workpiece by giving priority to repairing of a defective portion that is separated from the weld bead BD2 by more than the predetermined width.

The predetermined width is, for example, a designated length designated by a user based on a width of a weld bead defined before a main welding is started. When a defective portion (for example, the detected spot region AR1) is located within the designated length from the welding line WLN1, the repair welding device sets, as the repair welding section RPW1, a section from the start corresponding point Sh on the operation trajectory of the welding robot MC1 during a main welding corresponding to a start point (the start detected spot S1) of a defective portion region (the detected spot region AR1) included in an appearance inspection result to the end corresponding point Eh on the operation trajectory of the welding robot MC1 during the main welding corresponding to an end point (the end detected spot E1) of the defective portion region (the detected spot region AR1) included in the appearance inspection result. As a result, since a position where the detected spot region AR1 is detected is closer to the welding line WLN1 than the length designated by a user, the repair welding device can set a part of the operation trajectory of the welding robot MC1 as the repair welding section RPW1, and can execute a repair welding with high accuracy while efficiently moving the welding robot MC1 in the same manner as in a main welding. For example, during a repair welding, the repair welding device can prevent interference with a welded workpiece to be repaired and welded or a jig for fixing the welded workpiece, and thus can efficiently support smooth driving of the welding robot MC1.

The predetermined width is, for example, a designated length designated by a user based on a width of a weld bead defined before a main welding is started. When a defective portion (for example, the detected spot region AR2) is located outside the welding line WLN2 in a manner of exceeding the designated length, the repair welding device sets, as the repair welding section RPW2, a section from a start point (the start detected spot S2) of a defective portion region (the detected spot region AR2) included in an appearance inspection result to an end point (the end detected spot E2) of the defective portion region (the detected spot region AR2) included in the appearance inspection result. Accordingly, since a position where the detected spot region AR2 is detected is farther from the welding line WLN2 than the length designated by a user, the repair welding device can directly modify a part of the operation trajectory of the welding robot MC1 to a position of the detected spot region AR2 and set a repair welding section, and can appropriately execute a repair welding in which directly repairing of the detected spot region AR2 is prioritized over a movement on the operation trajectory of the welding robot MC1. For example, during a repair welding, although there is a risk of interference with a welded workpiece to be repaired and welded or a jig for fixing the welded workpiece, the repair welding device can improve a completion degree of a repaired and welded workpiece by giving priority to repairing of a defective portion that is separated from the weld bead BD2 by more than a predetermined width.

Second Embodiment

In the first embodiment, the repair welding program is generated by the inspection control device 3. In the second embodiment, an example in which the repair welding program is executed by the robot control device 2a will be described.

(Configuration of Welding System)

Figure 7:
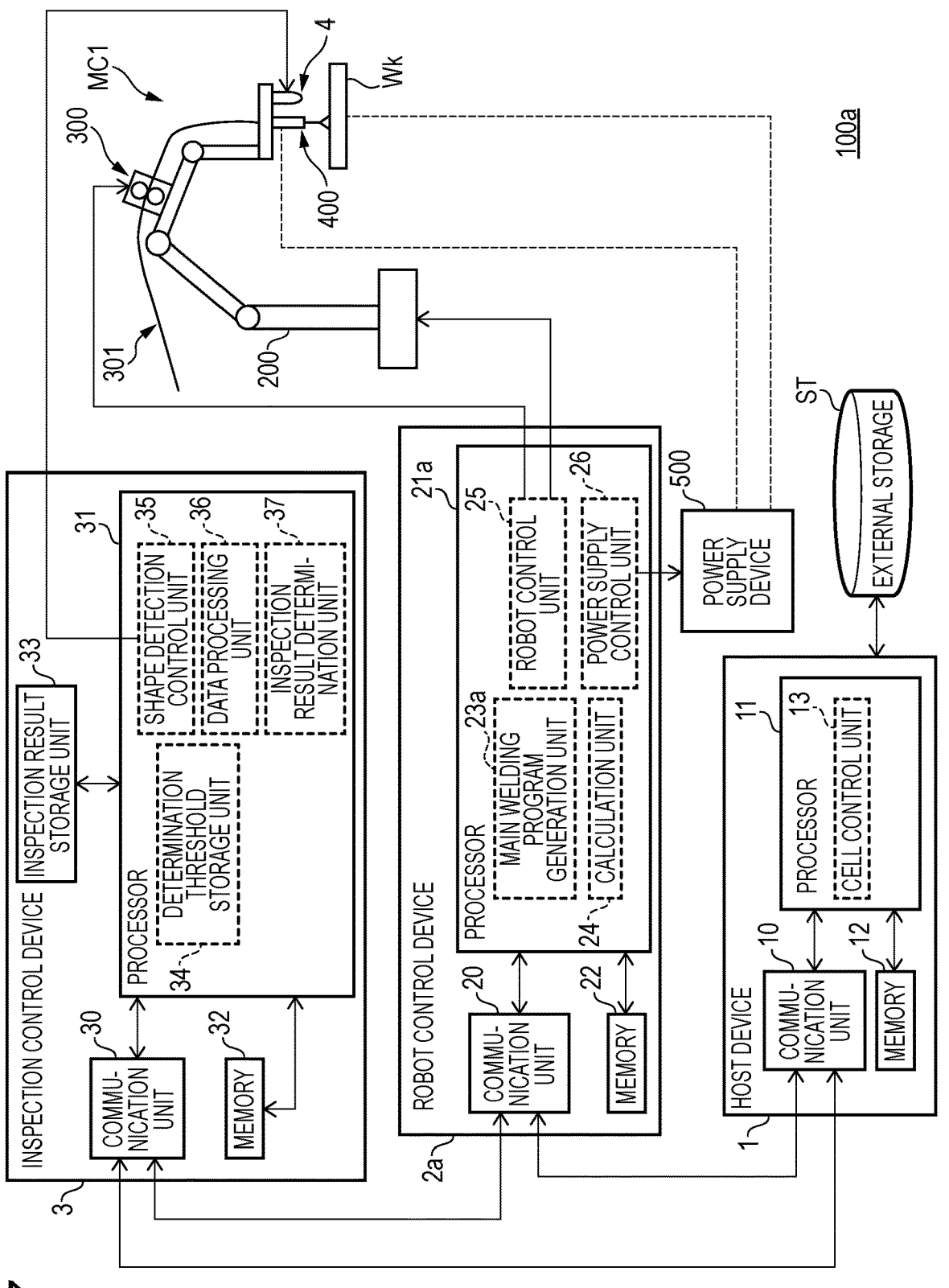
FIG. 7 is a diagram showing an internal configuration example of an inspection control device, a robot control device, and a host device according to a second embodiment.

FIG. 7 is a diagram showing an internal configuration example of the inspection control device 3, the robot control device 2a, and the host device 1 according to the second embodiment. In the description of FIG. 7, the same components as those shown in FIG. 2 are denoted by the same reference numerals, description thereof will be simplified or omitted, and different contents will be described. The configuration of a welding system 100a according to the second embodiment is the same as the configuration of the welding system 100 according to the first embodiment (see FIG. 1).

The robot control device 2a serving as an example of a repair welding device controls a processing of the corresponding welding robot MC1 (specifically, the manipulator 200, the wire feeding device 300, and the power supply device 500) based on a main welding execution command, a repair welding execution command, or an appearance inspection program execution command transmitted from the host device 1. The robot control device 2a includes at least the communication unit 20, a processor 21a, and the memory 22.

The processor 21a is configured with, for example, a CPU or an FPGA, and executes various processings and controls in cooperation with the memory 22. Specifically, the processor 21a implements functions of a main welding or repair welding program generation unit 23a, the calculation unit 24, the robot control unit 25, and the power supply control unit 26 by referring to a program stored in the memory 22 and executing the program.

The main welding or repair welding program generation unit 23a uses workpiece information (for example, an ID, a name, and a welded portion of an original workpiece) of each of a plurality of original workpieces included in a main welding execution command transmitted from the host device 1 via the communication unit 20 to generate a main welding program for a main welding to be executed by the welding robot MC1 based on the main welding execution command. The main welding or repair welding program generation unit 23a generates a repair welding program for a workpiece Wk (for example, a welded workpiece or a repaired and welded workpiece) to be executed by the welding robot MC1 by using the appearance inspection result of the workpiece Wk (for example, a welded workpiece or a repaired and welded workpiece) output from the inspection result determination unit 37 and workpiece information of a welded workpiece or a repaired and welded workpiece (for example, information such as coordinates indicating a position of a detected spot of a welding defect of a welded workpiece or a repaired and welded workpiece). Details of a procedure for creating the repair welding program are the same as those described in the first embodiment with reference to FIGS. 4, 5, and 6, and thus description thereof will be omitted. The generated main welding program and repair welding program may be stored in the processor 21a or may be stored in the RAM of the memory 22.

(Operation of Welding System)

Figure 8A:
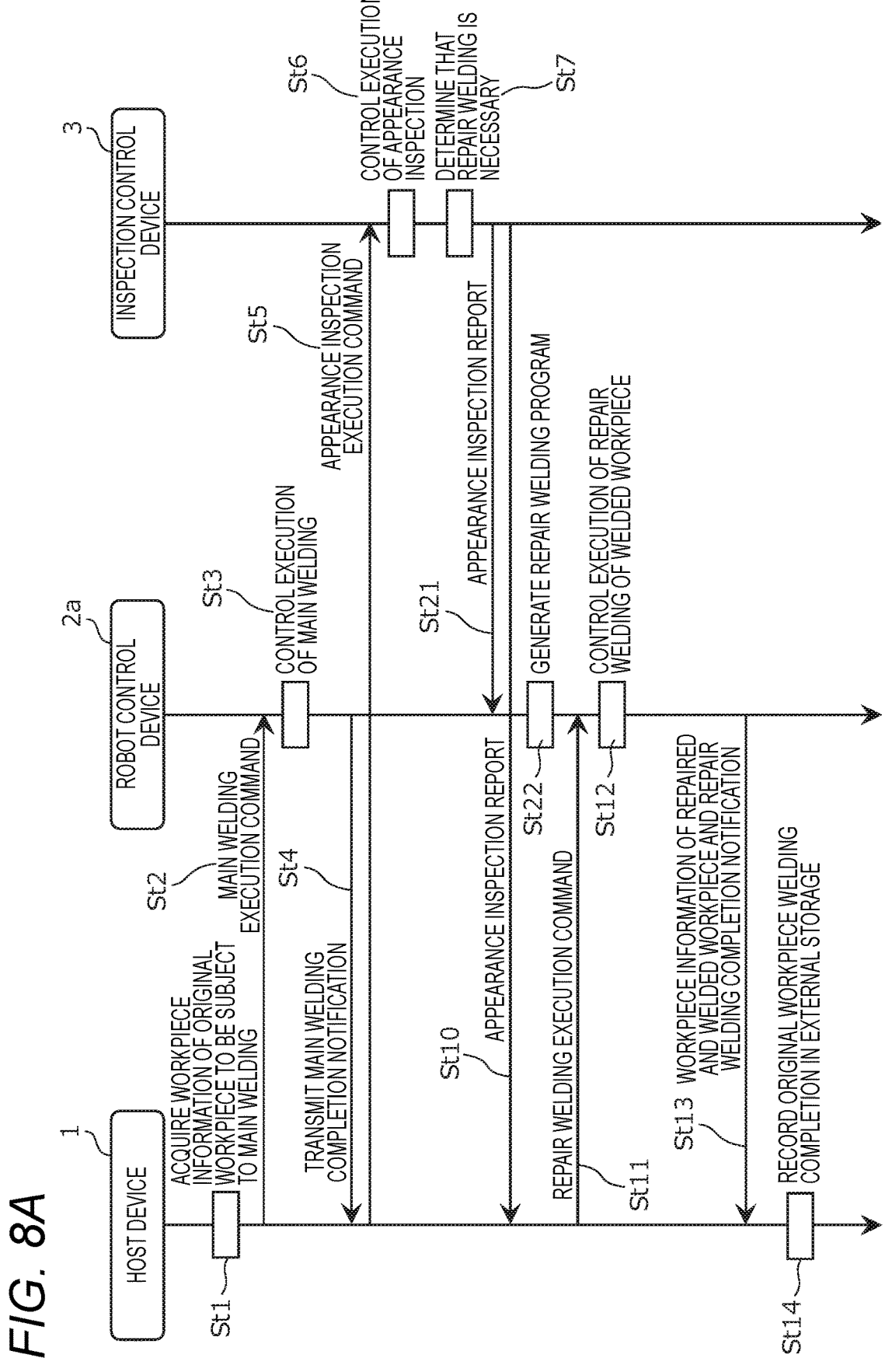
FIG. 8A is a sequence diagram showing an example of an operation procedure of a main welding and a repair welding that are executed by a welding system according to the second embodiment.
Figure 8B:
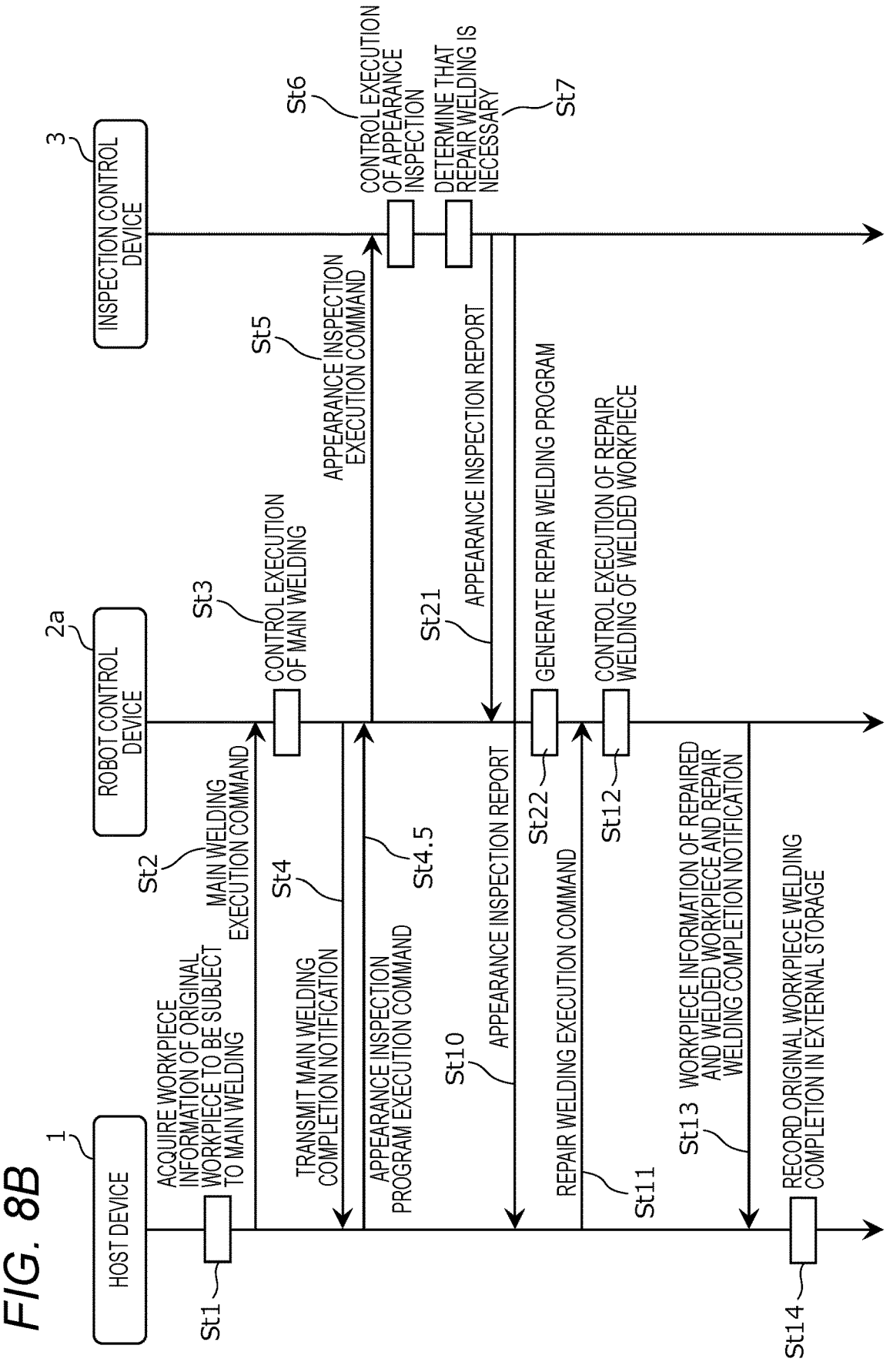
FIG. 8B is a sequence diagram showing a modification of the operation procedure of the main welding and the repair welding that are executed by the welding system according to the second embodiment.

Next, an operation procedure of a main welding and a repair welding that are executed by the welding system 100a according to the second embodiment will be described with reference to FIG. 8A. FIG. 8A is a sequence diagram showing an example of an operation procedure of a main welding and a repair welding that are executed by the welding system 100a according to the second embodiment. FIG. 8B is a sequence diagram showing a modification of the operation procedure of the main welding and the repair welding that are executed by the welding system 100a according to the second embodiment. In the description of FIGS. 8A and 8B, an operation procedure executed among the host device 1, the robot control device 2a, and the inspection control device 3 for each process of a main welding using a plurality of original workpieces and a repair welding executed based on a fact that an appearance inspection result of a welded workpiece is fail will be described as an example. In the description of FIG. 8A or FIG. 8B, the same step numbers are given to the same processes as those in FIG. 3A or FIG. 3B, description thereof will be simplified or omitted, and different contents will be described.

In FIG. 8A or FIG. 8B, the robot control device 2a may execute the processings of step St1 and step St2 without going through the host device 1. In this case, it is preferable that data the same as data stored in the external storage ST is stored in the memory 22 of the robot control unit 2a, or the robot control unit 2a is connected to the external storage ST so that the robot control device 2a can acquire data from the external storage ST. As shown in FIG. 8B, when the host device 1 receives the main welding completion notification, the host device 1 may generate an appearance inspection program execution command including an appearance inspection program of a welded workpiece and transmit the appearance inspection program execution command to the robot control device 2 (St4.5) in a similar manner to the processing shown in FIG. 3B. In this case, as shown in FIG. 8B, the robot control device 2a generates an appearance inspection execution command of the welded workpiece and transmits the appearance inspection execution command to the inspection control device 3 (St5), executes the appearance inspection program received from the host device 1 accompanying with the start of the appearance inspection, and moves the inspection device 4 attached to the welding robot MC1.

The inspection control device 3 executes an appearance inspection in cooperation with the inspection device 4 while the inspection device 4 is moved by the robot control device 2 so as to be able to scan a welded workpiece, determines that a repair welding is necessary because there is a welding defective portion in the welded workpiece as a result of the appearance inspection in step St6 (St7), generates an appearance inspection report including the determination result in step St7, and transmits the appearance inspection report to the robot control device 2a (St21). When the robot control device 2a receives the appearance inspection report transmitted in step St21, the robot control device 2a uses contents of the appearance inspection report (that is, the appearance inspection result) and the main welding program generated in step St3 to generate a repair welding program by modifying a part of the main welding program in the same manner as in the first embodiment (St22). When the robot control device 2a receives the repair welding execution command transmitted from the host device 1, the robot control device 2a causes the welding robot MC1 to execute a repair welding in accordance with the repair welding program based on the repair welding program (generated in step St22) for the welded workpiece designated by the repair welding execution command (St12). Processings after step St12 are the same as those in FIG. 3A, and thus description thereof will be omitted.

As described above, in the welding system 100a according to the second embodiment, the robot control device 2a uses the appearance inspection result to generate the repair welding program for executing a repair welding on a position of a defective portion. The repair welding device causes the welding robot MC1 to execute the repair welding on the defective portion in accordance with the generated repair welding program. Accordingly, the repair welding device can generate a repair welding program in which a repair welding section is set while improving operation efficiency of the welding robot MC1 based on a positional relationship between a detected spot region (for example, refer to FIG. 4 or FIG. 5) obtained in an appearance inspection and a weld bead, and can execute, with high accuracy, a repair welding in which repairing of a defective portion is prioritized based on the repair welding program.

Third Embodiment

In the second embodiment, the repair welding program is generated by the robot control device 2a. In the third embodiment, an example in which the repair welding program is executed by a host device 1a will be described.

(Configuration of Welding System)

Figure 9:
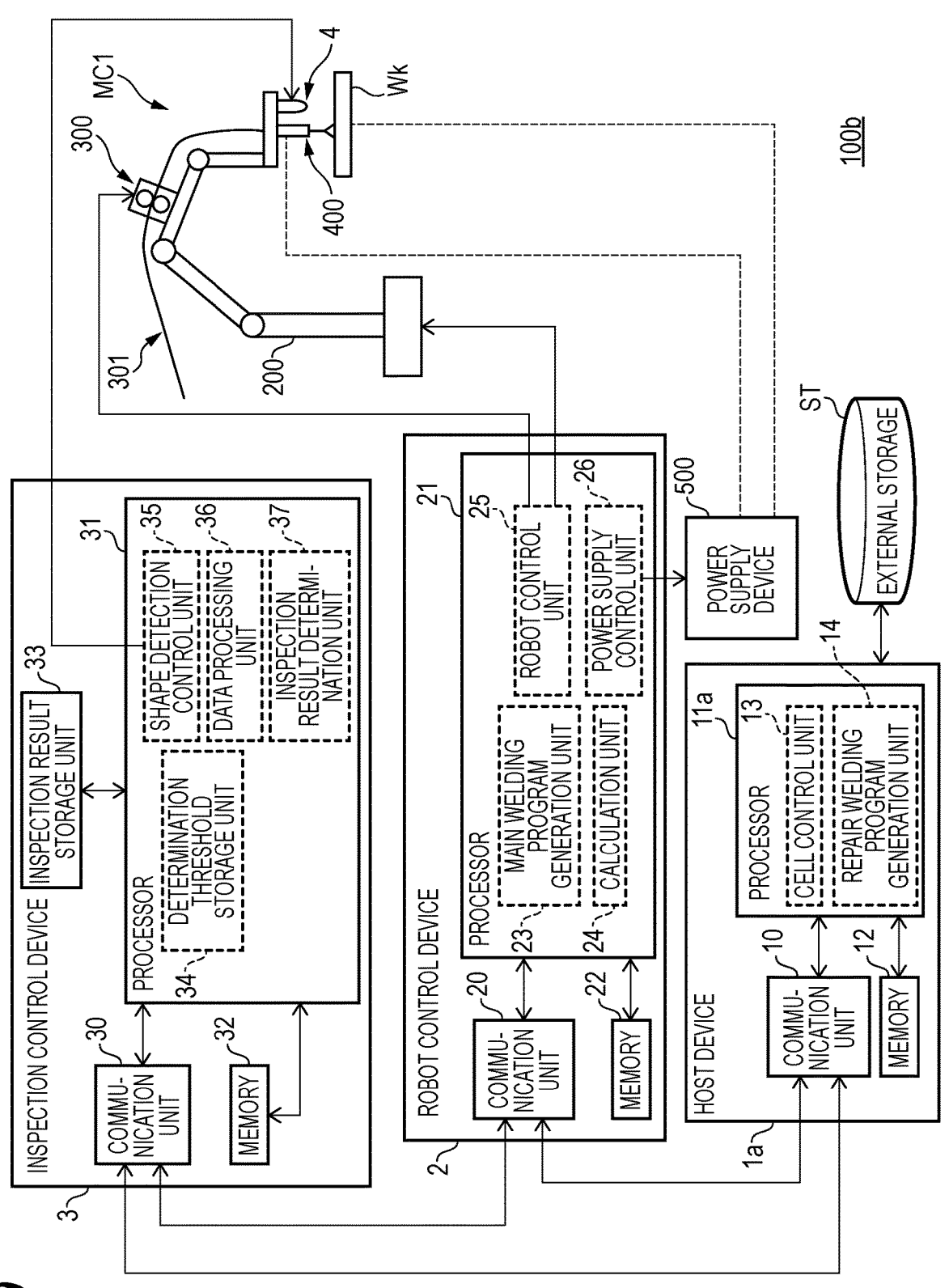
FIG. 9 is a diagram showing an internal configuration example of an inspection control device, a robot control device, and a host device according to a third embodiment.

FIG. 9 is a diagram showing an internal configuration example of the inspection control device 3, the robot control device 2, and the host device 1a according to the third embodiment. In the description of FIG. 9, the same components as those shown in FIG. 2 are denoted by the same reference numerals, description thereof will be simplified or omitted, and different contents will be described. The configuration of a welding system 100b according to the third embodiment is the same as the configuration of the welding system 100 according to the first embodiment (see FIG. 1).

The host device 1a serving as an example of a repair welding device integrally controls, via the robot control device 2, the execution of a repair welding (for example, start and completion of the repair welding) executed by the welding robot MC1. For example, when the host device 1a receives the appearance inspection report from the inspection control device 3, the host device 1a generates a repair welding program, generates a repair welding execution command for a welded workpiece produced by the welding robot MC1, and transmits the repair welding program to the robot control device 2. The host device 1a includes at least the communication unit 10, a processor 11a, and the memory 12.

The processor 11a is configured with, for example, a CPU or an FPGA, and executes various processings and controls in cooperation with the memory 12. Specifically, the processor 11a implements functions of the cell control unit 13 and the repair welding program generation unit 14 by referring to a program stored in the memory 12 and executing the program.

The repair welding program generation unit 14 generates a repair welding program for a workpiece Wk (for example, a welded workpiece or a repaired and welded workpiece) to be executed by the welding robot MC1 by using the appearance inspection result of the workpiece Wk (for example, a welded workpiece or a repaired and welded workpiece) transmitted from the inspection control device 3 and workpiece information of a welded workpiece or a repaired and welded workpiece (for example, information such as coordinates indicating a position of a detected spot of a welding defect of a welded workpiece or a repaired and welded workpiece). Details of a procedure for creating the repair welding program are the same as those described in the first embodiment with reference to FIGS. 4, 5, and 6, and thus description thereof will be omitted. The generated repair welding program may be stored in the processor 11a or in the RAM of the memory 12.

(Operation of Welding System)

Figure 10A:
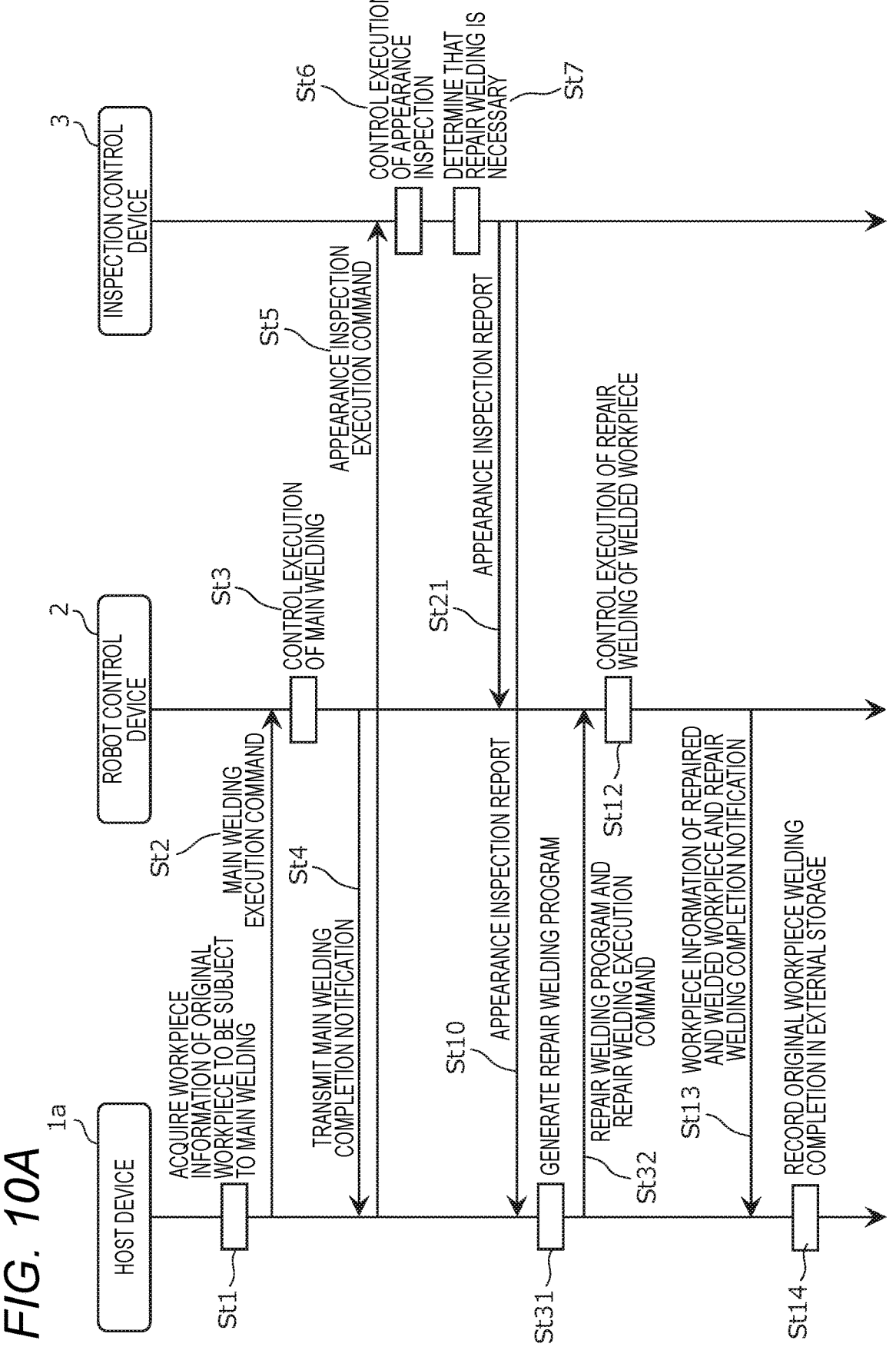
FIG. 10A is a sequence diagram showing an example of an operation procedure of a main welding and a repair welding that are executed by a welding system according to the third embodiment.
Figure 10B:
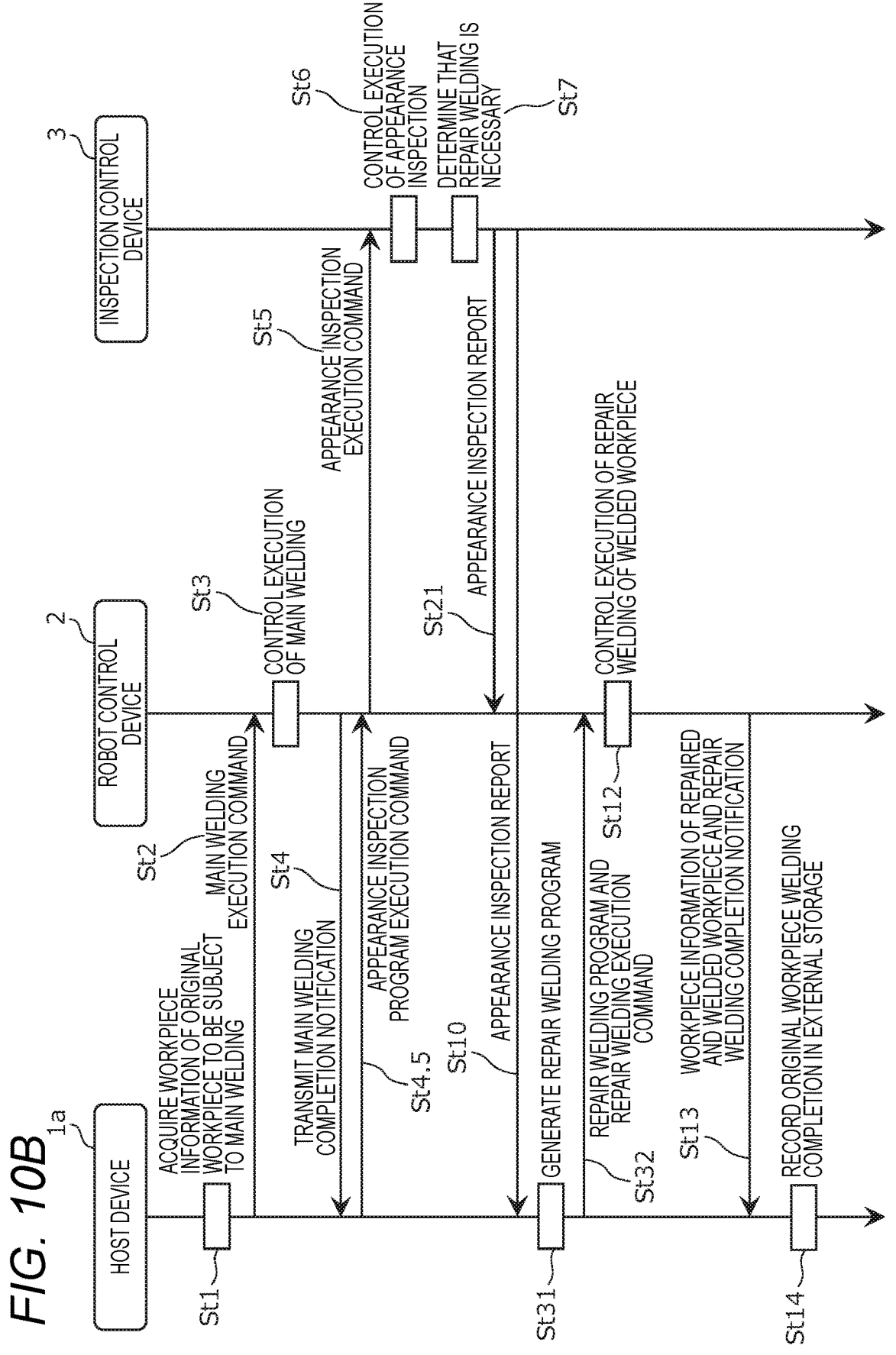
FIG. 10B is a sequence diagram showing a modification of the operation procedure of the main welding and the repair welding that are executed by the welding system according to the third embodiment.

Next, an operation procedure of a main welding and a repair welding that are executed by the welding system 100b according to the third embodiment will be described with reference to FIGS. 10A and 10B. FIG. 10A is a sequence diagram showing an example of an operation procedure of a main welding and a repair welding that are executed by the welding system 100b according to the third embodiment. FIG. 10B is a sequence diagram showing a modification of the operation procedure of the main welding and the repair welding that are executed by the welding system 100*b* according to the third embodiment. In the description of FIGS. 10A and 10B, an operation procedure executed among the host device 1*a*, the robot control device 2, and the inspection control device 3 for each process of a main welding using a plurality of original workpieces and a repair welding executed based on a fact that an appearance inspection result of a welded workpiece is fail will be described as an example. In the description of FIG. 10A or FIG. 10B, the same step numbers are given to the same processes as those in FIG. 3A or FIG. 3B, description thereof will be simplified or omitted, and different contents will be described.

In FIG. 10A or FIG. 10B, the robot control device 2 may execute the processings of step St1 and step St2 without going through the host device 1*a*. In this case, it is preferable that data the same as data stored in the external storage ST is stored in the memory 22 of the robot control unit 2, or the robot control unit 2 is connected to the external storage ST so that the robot control device 2 can acquire data from the external storage ST. As shown in FIG. 10B, when the host device 1*a* receives the main welding completion notification, the host device 1*a* may generate an appearance inspection program execution command including an appearance inspection program of a welded workpiece and transmit the appearance inspection program execution command to the robot control device 2 (St4.5) in a similar manner to the processing shown in FIG. 3B. In this case, as shown in FIG. 10B, the robot control device 2 generates an appearance inspection execution command of the welded workpiece and transmits the appearance inspection execution command to the inspection control device 3 (St5), executes the appearance inspection program received from the host device 1 a accompanying with the start of the appearance inspection, and moves the inspection device 4 attached to the welding robot MC1.

The inspection control device 3 determines that a repair welding is necessary because there is a welding defective portion in the welded workpiece as a result of the appearance inspection in step St6 (St7), generates an appearance inspection report including the determination result in step St7 and transmits the appearance inspection report to the robot control device 2 (St21). The inspection control device 3 transmits the appearance inspection report generated in the same manner to the host device 1*a* (St10).

When the host device 1*a* receives the appearance inspection report transmitted in step St10, the host device 1*a* acquires the main welding program from the robot control device 2, and uses contents of the appearance inspection report (that is, the appearance inspection result) and the main welding program to generate a repair welding program by modifying a part of the main welding program in the same manner as in the first embodiment (St31). Although not shown in detail in FIG. 10A, when the inspection control device 3 receives the appearance inspection report transmitted in step St 10, the inspection control device 3 may request data of the main welding program from the robot control device 2 and acquire the data of the main welding program transmitted from the robot control device 2 in response to the request, or may acquire the data of the main welding program transmitted from the robot control device 2 after the step St3 in advance. Accordingly, the host device 1 a can efficiently generate data of the repair welding program by partially modifying the acquired data of the main welding program. The host device 1*a* transmits the repair welding program that is generated by generating a repair welding execution command for a welded workpiece to the robot control device 2 (St32). When the robot control device 2 receives the repair welding execution command transmitted from the host device 1*a*, the robot control device 2 causes the welding robot MC1 to execute a repair welding in accordance with the repair welding program based on the repair welding program (received in step St32) for the welded workpiece designated by the repair welding execution command (St12). Processings after step St12 are the same as those in FIG. 3A, and thus description thereof will be omitted.

As described above, in the welding system 100*b* according to the third embodiment, the host device 1*a* uses the appearance inspection result to generate the repair welding program for executing a repair welding on a position of a defective portion. The repair welding device causes the welding robot MC1 to execute the repair welding on the defective portion in accordance with the generated repair welding program. Accordingly, the repair welding device can generate a repair welding program in which a repair welding section is set while improving operation efficiency of the welding robot MC1 based on a positional relationship between a detected spot region (for example, refer to FIG. 4 or FIG. 5) obtained in an appearance inspection and a weld bead, and can execute, with high accuracy, a repair welding in which repairing of a defective portion is prioritized based on the repair welding program.

Although various embodiments are described above with reference to the drawings, it is needless to say that the present disclosure is not limited to such examples. It will be apparent to those skilled in the art that various changes, modifications, substitutions, additions, deletions, and equivalents can be conceived within the scope of the claims, and it should be understood that such changes and the like also belong to the technical scope of the present disclosure. Components in various embodiments described above may be combined freely in a range without deviating from the spirit of the invention.

The present disclosure is useful as a repair welding device and a repair welding method for more efficiently repairing and welding a defective portion of a welded workpiece produced by a main welding.

What is claimed is:

1. A repair welding device comprising:
an inspection result acquisition unit configured to acquire an appearance inspection result including information about a defective portion of a weld bead of a welded workpiece produced by a main welding that is executed by a welding robot;
a robot control unit configured to instruct the welding robot to execute a repair welding on a position of the defective portion using the appearance inspection result based on a relationship between the position of the defective portion and a predetermined width related to the weld bead; and
a repair welding program generation unit configured to generate a repair welding program comprising instructions for:
executing the repair welding on a corresponding position on a welding line in a same manner as a main welding program, in a case that the defective portion is located at a position where a distance of the defective portion from the welding line is within the predetermined width; and
executing the repair welding by modifying a part of an operational trajectory to the position of the defective portion, thereby directly repairing the defective portion, in a case that the defective portion is farther from the welding line than the predetermined width.

2. The repair welding device according to claim 1,
wherein the robot control unit causes the welding robot to execute the repair welding on the defective portion in accordance with the repair welding program.

3. The repair welding device according to claim 2,
wherein the predetermined width is a half width equivalent length of the weld bead, and
wherein the repair welding program generation unit sets, as a repair welding section, a section from a start corresponding point on an operation trajectory of the welding robot during the main welding corresponding to a start point of a defective portion region included in the appearance inspection result to an end corresponding point on the operation trajectory of the welding robot during the main welding corresponding to an end point of the defective portion region included in the appearance inspection result, in a case that the defective portion is located within the half width equivalent length from the welding line in the main welding.

4. The repair welding device according to claim 2,
wherein the predetermined width is a half width equivalent length of the weld bead, and
wherein the repair welding program generation unit sets, as a repair welding section, a section from a start point of a defective portion region included in the appearance inspection result to an end point of the defective portion region included in the appearance inspection result in a case that the defective portion is located at a position exceeding the half width equivalent length from the from a welding line in the main welding.

5. The repair welding device according to claim 2,
wherein the predetermined width is a designated length designated by a user based on a width of the weld bead defined before the main welding is started, and
wherein the repair welding program generation unit sets, as a repair welding section, a section from a start corresponding point on an operation trajectory of the welding robot during the main welding corresponding to a start point of a defective portion region included in the appearance inspection result to an end corresponding point on the operation trajectory of the welding robot during the main welding corresponding to an end point of the defective portion region included in the appearance inspection result, in a case that the defective portion is located within the designated length from the welding line in the main welding.

6. The repair welding device according to claim 2,
wherein the predetermined width is a designated length designated by a user based on a width of the weld bead defined before the main welding is started, and
wherein the repair welding program generation unit sets, as a repair welding section, a section from a start point of a defective portion region included in the appearance inspection result to an end point of the defective portion region included in the appearance inspection result in a case that the defective portion is located at a position exceeding the designated length from the welding line in the main welding.

7. A repair welding method to be executed by a repair welding device, the repair welding method comprising:
acquiring an appearance inspection result including information about a defective portion of a weld bead of a welded workpiece produced by a main welding that is executed by a welding robot;
instructing the welding robot to execute a repair welding on a position of the defective portion using the appearance inspection result based on a relationship between the position of the defective portion and a predetermined width related to the weld bead; and
generating a repair welding program comprising instructions for:
executing the repair welding on a corresponding position on a welding line in a same manner as a main welding program, in a case that the defective portion is located at a position where a distance of the defective portion from the welding line is within the predetermined width; and
executing the repair welding by modifying a part of an operational trajectory to the position of the defective portion, thereby directly repairing the defective portion, in a case that the defective portion is farther from the welding line than the predetermined width.

* * * * *